(12) United States Patent
Manetsch et al.

(10) Patent No.: US 10,323,007 B1
(45) Date of Patent: Jun. 18, 2019

(54) $N^2N$ $N^4$-DISUBSTITUTED QUINAZOLINE-2,4-DIAMINES AND USES THEREOF

(71) Applicants: Roman Manetsch, Boston, MA (US); Kurt S. Van Horn, Venice, FL (US); Whittney Burda, Tampa, FL (US); Lindsey N. Shaw, Tampa, FL (US); Renee Fleeman, Tampa, FL (US); Megan Barber, Parrish, FL (US); David Lawrence Flanigan, Riverview, FL (US)

(72) Inventors: Roman Manetsch, Boston, MA (US); Kurt S. Van Horn, Venice, FL (US); Whittney Burda, Tampa, FL (US); Lindsey N. Shaw, Tampa, FL (US); Renee Fleeman, Tampa, FL (US); Megan Barber, Parrish, FL (US); David Lawrence Flanigan, Riverview, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 15/703,651

(22) Filed: Sep. 13, 2017

Related U.S. Application Data

(60) Provisional application No. 62/393,938, filed on Sep. 13, 2016.

(51) Int. Cl.
  *C07D 239/95* (2006.01)
  *A61P 31/04* (2006.01)
  *C07D 405/04* (2006.01)

(52) U.S. Cl.
  CPC ......... *C07D 239/95* (2013.01); *C07D 405/04* (2013.01)

(58) Field of Classification Search
  CPC .................................................. C07D 239/95
  See application file for complete search history.

(56) References Cited

U.S. PATENT DOCUMENTS 8,906,918 B1 * 12/2014 Manetsch ............ C07D 239/95
  514/241
2009/0004185 A1   1/2009 Venkatesan et al.

OTHER PUBLICATIONS

Ekins et al. Pharm Res (2014) 31:414-435.*
Perez, F.; Hujer, A. M.; Hujer, K. M.; Decker, B. K.; Rather, P. N.; Bonomo, R. A., Global Challenge of Multidrug-Resistant Acinetobacter baumannii. Antimicrobial Agents and Chemotherapy 2007, 51 (10), 3471-3484.
Hakyemez, I., Kucukbayrak, A., Tas, Tekin, Yikilgan, A., Akkaya A., Yasayacak, A., Akdeniz, H., Nosocomial Acinetobacter bauman-nii Infections and Changing Antibiotic Resistance. Pak J Med Sci 2013, 29 (5), 1245-8.
Sebeny, Peter J.; Riddle, Mark S.; Petersen, K., Acinetobacter baumanniiSkin and Soft-Tissue Infection Associated with War Trauma. Clinical Infectious Diseases 2008, 47 (4), 444-449.
Akers, K. S.; Mende, K.; Cheatle, K. A.; Zera, W. C.; Yu, X.; Beckius, M. L.; Aggarwal, D.; Li, P.; Sanchez, C. J.; Wenke, J. C.; Weintrob, A. C.; Tribble, D. R.; Murray, C. K., Biofilms and persistent wound infections in United States military trauma patients: a case-control analysis. BMC Infectious Diseases 2014, 14 (1), 190, pp. 1-11.
Manchanda, V.; Sanchaita, S.; Singh, N., Multidrug resistant acinetobacter. J Glob Infect Dis 2010, 2 (3), 291-304.
Boucher, Helen W.; Talbot, George H.; Bradley, John S.; Edwards, John E.; Gilbert, D.; Rice, Louis B.; Scheld, M.; Spellberg, B.; Bartlett, J., Bad Bugs, No Drugs: No ESKAPE! An Update from the Infectious Diseases Society of America. Clinical Infectious Diseases 2009, 48 (1), 1-12.
Falagas, M. E.; Bliziotis, I. A., Pandrug-resistant Gram-negative bacteria: the dawn of the post-antibiotic era? International Journal of Antimicrobial Agents 2007, 29 (6), 630-636.
Van Horn, K. S.; Zhu, X.; Pandharkar, T.; Yang, S.; Vesely, B.; Vanaerschot, M.; Dujardin, J.-C.; Rijal, S.; Kyle, D. E.; Wang, M. Z.; Werbovetz, K. A.; Manetsch, R., Antileishmanial Activity of a Series of N2,N4-Disubstituted Quinazoline-2,4-diamines. Journal of medicinal chemistry 2014, 57 (12), 5141-5156.
Zhu, X.; Van Horn, K. S.; Barber, M. M.; Yang, S.; Wang, M. Z.; Manetsch, R.; Werbovetz, K. A., SAR refinement of antileishmanial N2,N4-disubstituted quinazoline-2,4-diamines. Bioorganic & medicinal chemistry 2015, 23 (16), 5182-5189.
Wang, D.; Gao, F., Quinazoline derivatives: synthesis and bioactivities. Chem Cent J 2013, 7 (1), 95, pp. 1-15.
Alagarsamy, V.; Raja Solomon, V.; Dhanabal, K., Synthesis and pharmacological evaluation of some 3-phenyl-2-substituted-3H-quinazolin-4-one as analgesic, anti-inflammatory agents. Bioorganic & Medicinal Chemistry 2007, 15 (1), 235-241.
Chandregowda, V.; Kush, A. K.; Chandrasekara Reddy, G., Synthesis and in vitro antitumor activities of novel 4-anilinoquinazoline derivatives. European Journal of Medicinal Chemistry 2009, 44 (7), 3046-3055.
Rohini, R.; Muralidhar Reddy, P.; Shanker, K.; Hu, A.; Ravinder, V., Antimicrobial study of newly synthesized 6-substituted indolo[1,2-c]quinazolines. European Journal of Medicinal Chemistry 2010, 45 (3), 1200-1205.
Alvarado, M.; Barceló, M.; Carro, L.; Masaguer, C. F.; Raviña, E., Synthesis and Biological Evaluation of New Quinazoline and Cinnoline Derivatives as Potential Atypical Antipsychotics. Chemistry & Biodiversity 2006, 3 (1), 106-117.

(Continued)

*Primary Examiner* — Emily A Bernhardt
(74) *Attorney, Agent, or Firm* — Thomas|Horstemeyer, LLP

(57) ABSTRACT

Described herein are quinazoline-based compounds and formulations thereof. In some embodiments, the compounds and/or formulations thereof can be effective to inhibit and/or kill *A. baumannii*. Also described herein are methods of treating a subject in need thereof by administering to the subject in need thereof a quinazoline-based compound and/or formulation thereof to the subject in need thereof.

6 Claims, 4 Drawing Sheets

(56) References Cited

OTHER PUBLICATIONS

Malamas, M. S.; Millen, J., Quinazolineacetic acids and related analogs as aldose reductase inhibitors. Journal of Medicinal Chemistry 1991, 34 (4), 1492-1503.

Kung, P. P.; Casper, M. D.; Cook, K. L.; Wilson-Lingardo, L.; Risen, L. M.; Vickers, T. A.; Ranken, R.; Blyn, L. B.; Wyatt, J. R.; Cook, P. D.; Ecker, D. J., Structure-activity relationships of novel 2-substituted quinazoline antibacterial agents. J Med Chem 1999, 42 (22), 4705-4713.

Harris, N. V.; Smith, C.; Bowden, K., Antifolate and antibacterial activities of 5-substituted 2,4-diaminoquinazolines. J Med Chem 1990, 33 (1), 434-444.

Van Horn, K. S.; Burda, W. N.; Fleeman, R.; Shaw, L. N.; Manetsch, R., Antibacterial Activity of a Series of N2,N4-Disubstituted Quinazoline-2,4-diamines. Journal of Medicinal Chemistry 2014, 57 (7), 3075-3093.

Lam, T.; Hilgers, M. T.; Cunningham, M. L.; Kwan, B. P.; Nelson, K. J.; Brown-Driver, V.; Ong, V.; Trzoss, M.; Hough, G.; Shaw, K. J.; Finn, J., Structure-Based Design of New Dihydrofolate Reductase Antibacterial Agents: 7-(Benzimidazol-1-yl)-2,4-diaminoquinazolines. Journal of Medicinal Chemistry 2014, 57 (3), 651-668.

DeGraw, J. I.; Brown, V. H.; Colwell, W. T.; Morrison, N. E., Potential antileprotic agents. 3. Inhibition of mycobacterial dihydrofolic reductase by 2,4-diamino-5-methyl-6-alkylquinazolines. Journal of Medicinal Chemistry 1974, 17 (7), 762-764.

Blaney, J. M.; Hansch, C.; Silipo, C.; Vittoria, A., Structure-activity relationships of dihydrofolated reductase inhibitors. Chemical Reviews 1984, 84 (4), 333-407.

Miyaura, N.; Suzuki, A., Palladium-Catalyzed Cross-Coupling Reactions of Organoboron Compounds. Chemical Reviews 1995, 95 (7), 2457-2483.

Cormier, R.; Burda, W. N.; Harrington, L.; Edlinger, J.; Kodigepalli, K. M.; Thomas, J.; Kapolka, R.; Roma, G.; Anderson, B. E.; Turos, E.; Shaw, L. N., Studies on the antimicrobial properties of N-acylated ciprofloxacins. Bioorganic & medicinal chemistry letters 2012, 22 (20), 6513-6520.

Fleeman, R. et al., Combinatorial Libraries As a Tool for the Discovery of Novel, Broad-Spectrum Antibacterial Agents Targeting the ESKAPE Pathogens. Journal of medicinal chemistry 2015, pp. 3340-3355.

Burda, W. N.; Fields, K. B.; Gill, J. B.; Burt, R.; Shepherd, M.; Zhang, X. P.; Shaw, L. N., Neutral metallated and meso-substituted porphyrins as antimicrobial agents against Gram-positive pathogens. European Journal of Clinical Microbiology & Infectious Diseases 2011, 31 (3), 327-335.

Von Salm, J. L.; Witowski, C. G.; Fleeman, R. M.; McClintock, J. B.; Amsler, C. D.; Shaw, L. N.; Baker, B. J., Darwinolide, a New Diterpene Scaffold That Inhibits Methicillin-Resistant *Staphylococcus aureus* Biofilm from the Antarctic Sponge Dendrilla membranosa. Org Lett 2016, 18 (11), 2596-2599.

Jacobs, A. C.; et al. Inactivation of Phospholipase D Diminishes Acinetobacter baumannii Pathogenesis. Infection and Immunity 2010, 78 (5), 1952-1962.

\* cited by examiner

$N^2N$ $N^4$-DISUBSTITUTED QUINAZOLINE-2,4-DIAMINES AND USES THEREOF

CROSS-REFERENCE TO RELATED APPLICATIONS

This application claims the benefit of and priority to U.S. Provisional Patent Application No. 62/393,938, filed on Sep. 13, 2016, entitled "CHARACTERIZING THE ANTIMICROBIAL ACTIVITY OF N2,N4-DISUBSTITUTED QUINAZOLINE-2,4-DIAMINES TOWARDS MULTIDRUG RESISTANT *ACINETOBACTER BAUMANNII*," the contents of which is incorporated by reference herein in its entirety.

STATEMENT REGARDING FEDERALLY SPONSORED RESEARCH OR DEVELOPMENT

This invention was made with government support under grant numbers AI103715 and AI80626 awarded by the National Institutes of Health. The government has certain rights in the invention.

BACKGROUND

Antibiotics and other drugs have been used for over seven decades to treat infectious diseases. And while they have significantly reduced illness and death, these compounds have been used so widely and for so long that the infectious organisms that many infectious organisms have developed resistance to the currently available drugs. Bacterial drug resistance is a significant problem world-wide. In the United States alone, at least 2 million people become infected with bacteria that are resistant to antibiotics, which directly results in about 23,000 deaths. As such, there is an immediate need for new compounds that are effective against infectious organisms.

SUMMARY

Described herein are compounds that can have a structure according to Formula 1:

Formula 1

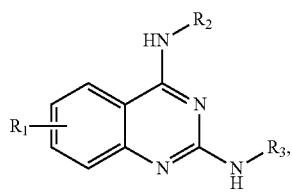

wherein $R_1$ can be selected from the group of:
6-Cl, 7-Cl, 6-Br, 7-Br, 6-Me, 7-Me, 6-OMe, 6-H, (6-H, 7-H),

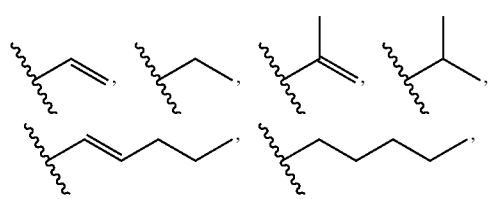

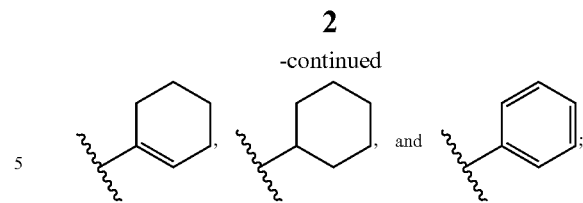

wherein $R_2$ can be selected from the group of: $CH_3$ and

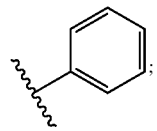 [SMILES: *c1ccccc1]

and wherein $R_3$ can be selected from the group of:

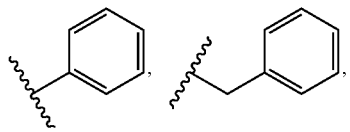

and $CH_3$.

In some embodiments, $R_1$ can be selected from the group of: 6-Br, 7-Br, 6-Me, 7-Me, (6-H, 7-H), 6-H, 6-Cl, and 6-OMe; wherein $R_2$ can be $CH_3$; and wherein $R_3$ can be

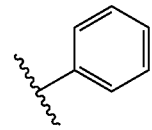 [SMILES: *c1ccccc1]

or

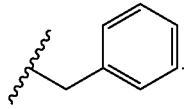

In some embodiments, $R_1$ can be selected from the group of: 6-Br, 6-Me, 7-Br, 7-Me, (6-H, 7-H); wherein $R_2$ can be $CH_3$; and wherein $R_3$ can be

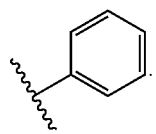

In some embodiments, $R_1$ can be selected from the group of: 6-H, 6-Cl, 6-OMe, 6-Br, and 6-Me; $R_2$ can be $CH_3$; and $R_3$ can be

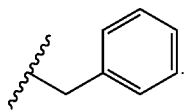

In some embodiments, $R_1$ can be selected from the group of: 6-Me,

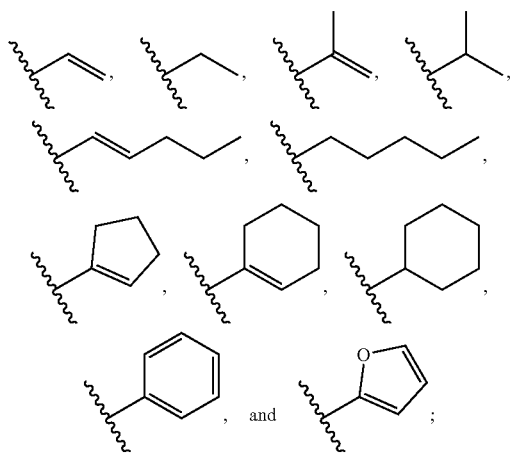

, and

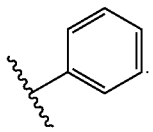 [SMILES: *c1ccccc1]

;

$R_2$ can be $CH_3$; and $R_3$ can be

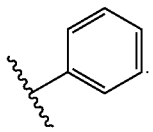 [SMILES: *c1ccccc1]

.

In some embodiments, $R_1$ can be selected from the group of: 6-Cl, 6-Br, 6-Me, 6-OMe, 7-Cl, 7-Br, and 7-Me; $R_2$ can be

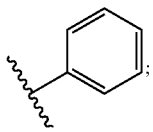

;

and $R_3$ can be $CH_3$.

In some embodiments, $R_1$ can be 6-Me; $R_2$ can be $CH_3$; and wherein $R_3$ can be

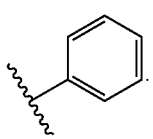 [SMILES: *c1ccccc1]

.

Also described herein are pharmaceutical formulations that can include a compound that can have a structure according to Formula 1:

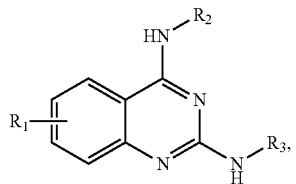

Formula 1 wherein $R_1$ can be selected from the group of: 6-Cl, 7-Cl, 6-Br, 7-Br, 6-Me, 7-Me, 6-OMe, 6-H, (6-H, 7-H),

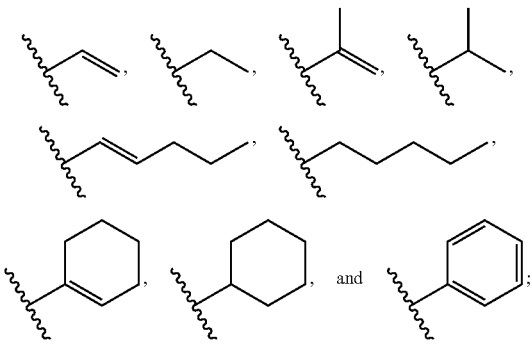

, and

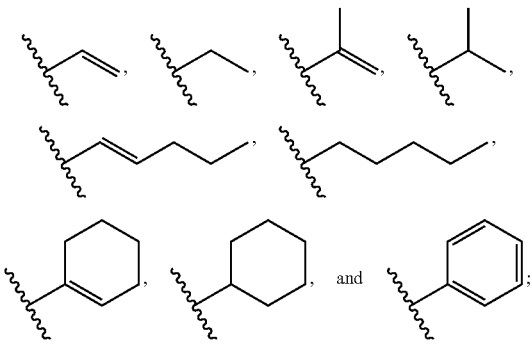

;

wherein $R_2$ can be selected from the group of: $CH_3$ and

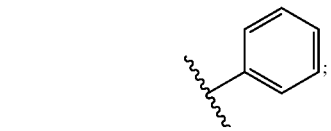 [SMILES: *c1ccccc1]

;

and wherein $R_3$ can be selected from the group of:

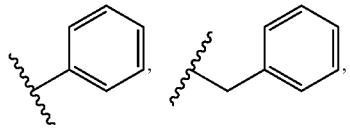

and $CH_3$; and a pharmaceutically acceptable carrier.

In some embodiments, $R_1$ can be selected from the group of: 6-Br, 7-Br, 6-Me, 7-Me, (6-H, 7-H), 6-H, 6-Cl, and 6-OMe; $R_2$ can be $CH_3$; and $R_3$ can be

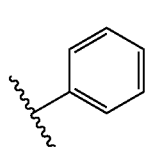 [SMILES: *c1ccccc1]

or

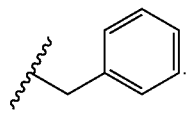

In some embodiments, $R_1$ can be selected from the group of: 6-Br, 6-Me, 7-Br, 7-Me, (6-H, 7-H); $R_2$ can be $CH_3$; and wherein $R_3$ can be

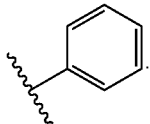 [SMILES: *c1ccccc1]

In some embodiments, $R_1$ can be selected from the group of: 6-H, 6-Cl, 6-OMe, 6-Br, and 6-Me; $R_2$ can be $CH_3$; and $R_3$ can be

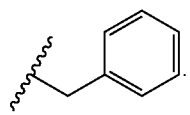 [SMILES: *Cc1ccccc1]

In some embodiments, $R_1$ can be selected from the group of: 6-Me,

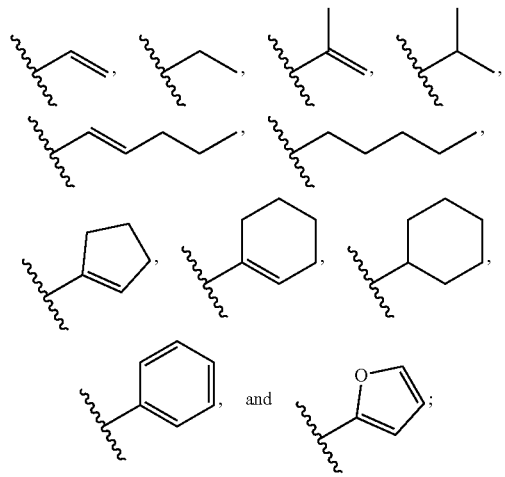

$R_2$ can be $CH_3$; and wherein $R_3$ can be

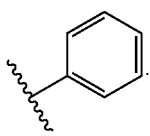 [SMILES: *c1ccccc1]

In some embodiments, $R_1$ can be selected from the group of: 6-Cl, 6-Br, 6-Me, 6-OMe, 7-Cl, 7-Br, and 7-Me; $R_2$ can be

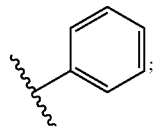 [SMILES: *c1ccccc1]

and $R_3$ can be $CH_3$.

In some embodiments, $R_1$ can be 6-Me; $R_2$ can be CH3; and $R_3$ can be

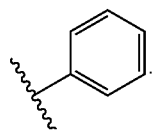 [SMILES: *c1ccccc1]

Also described herein are methods of treating *A. baumannii* infection in a subject in need thereof that can include the step of administering an amount of a compound that can have a structure according to Formula 1:

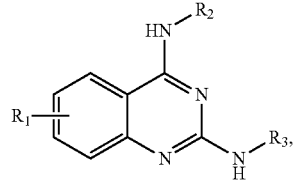

Formula 1 wherein $R_1$ can be selected from the group of: 6-Cl, 7-Cl, 6-Br, 7-Br, 6-Me, 7-Me, 6-OMe, 6-H, (6-H, 7-H),

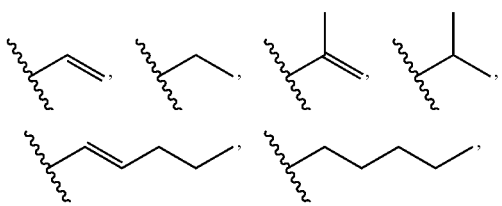

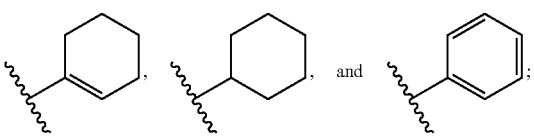

wherein $R_2$ can be selected from the group of: $CH_3$ and

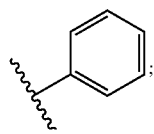

and wherein R$_3$ can be selected from the group of

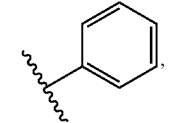,

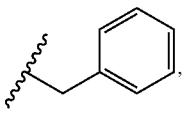 [SMILES: *Cc1ccccc1], and CH$_3$.

In some embodiments, R$_1$ can be selected from the group of: 6-Br, 7-Br, 6-Me, 7-Me, (6-H, 7-H), 6-H, 6-Cl, and 6-OMe; R$_2$ can be CH$_3$; and R$_3$ can be

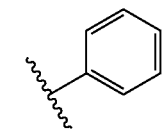

or

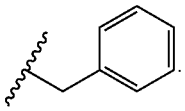 [SMILES: *Cc1ccccc1].

In some embodiments, R$_1$ can be selected from the group of: 6-Br, 6-Me, 7-Br, 7-Me, (6-H, 7-H); R$_2$ can be CH$_3$; and R$_3$ can be

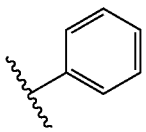.

In some embodiments, R$_1$ can be selected from the group of: 6-H, 6-Cl, 6-OMe, 6-Br, and 6-Me; R$_2$ can be CH$_3$; and R$_3$ can be

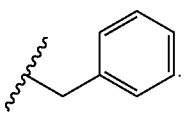.

In some embodiments, R$_1$ can be selected from the group of: 6-Me,

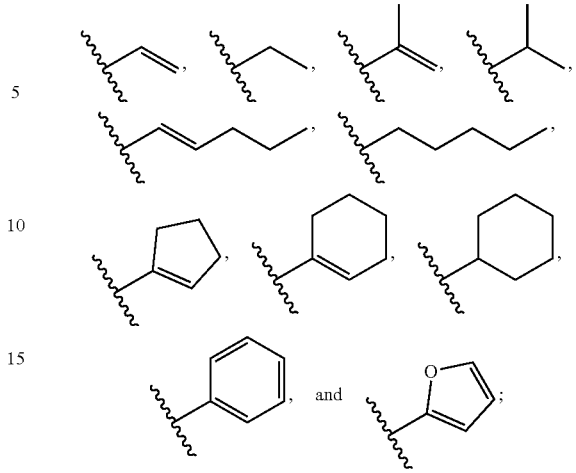

R$_2$ can be CH$_3$; and R$_3$ can be

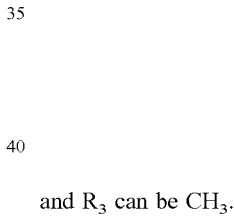.

In some embodiments, R$_1$ can be selected from the group of: 6-Cl, 6-Br, 6-Me, 6-OMe, 7-Cl, 7-Br, and 7-Me; R$_2$ can be

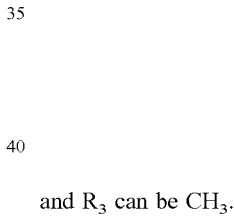;

and R$_3$ can be CH$_3$.

BRIEF DESCRIPTION OF THE DRAWINGS

Further aspects of the present disclosure will be readily appreciated upon review of the detailed description of its various embodiments, described below, when taken in conjunction with the accompanying drawings.

DETAILED DESCRIPTION

Figure 1:
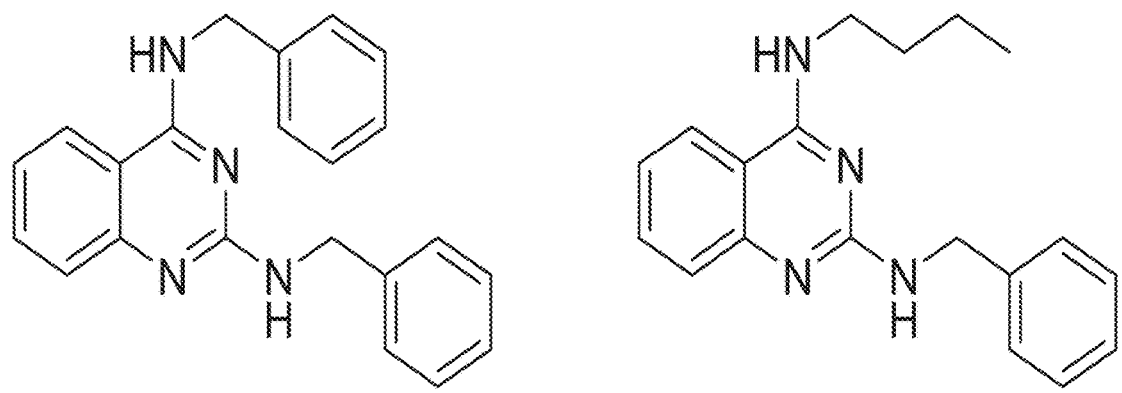
FIG. 1 shows N$^2$,N$^4$-disubstituted quinazolin-2,4-diamines with potent anti-MRSA activity.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of biology, microbiology, organic chemistry, biochemistry, chemistry, and the like, which are within the skill of the art. Such techniques are explained fully in the literature.

Definitions

As used herein, "about," "approximately," and the like, when used in connection with a numerical variable, can refer to the value of the variable and to all values of the variable that are within the experimental error (e.g., within the 95% confidence interval for the mean) or within +/−10% of the indicated value, whichever is greater.

As used herein, "additive effect" can refer to an effect arising between two or more molecules, compounds, substances, factors, or compositions that is equal to or the same as the sum of their individual effects.

As used herein, "administering" can refer to any administration route, including but not limited to, administration that is oral, topical, intravenous, subcutaneous, transcutaneous, transdermal, intramuscular, intra-articular, parenteral, intra-arterial, intradermal, intraventricular, intracranial, intraperitoneal, intralesional, intranasal, rectal, vaginal, by inhalation, or via an implanted reservoir. The term "parenteral" includes subcutaneous, intravenous, intramuscular, intra-articular, intra-synovial, intrasternal, internasal, intrathecal, intrahepatic, intralesional, and intracranial injections or infusion techniques.

As used interchangeably herein, "biocompatible," "biocompatibility," and "biologically compatible" can refer to materials that are, with any metabolites or degradation products thereof, generally non-toxic to the recipient, and cause no significant adverse effects to the recipient. Generally speaking, biocompatible materials are materials which do not elicit a significant inflammatory or immune response when administered to a patient. In some embodiments, a biocompatible material elicits no detectable change in one or more biomarkers indicative of an immune response. In some embodiments, a biocompatible material elicits no greater than a 10% change, no greater than a 20% change, or no greater than a 40% change in one or more biomarkers indicative of an immune response.

As used herein, "a compound of formula (1), (2), (3), (4), (5), (6), (6a), (6b) (7), (8), (9), (10), (11), (12), (13), (14), (A), (B), (C), (D), and so forth and so on," or "a compound having a structure according to formula (1), (2), (3), (4), (5), (6), (6a), (6b) (7), (8), (9), (10), (11), (12), (13), (14), (A), (B), (C), (D), etc.," compound (1), (2), (3), (4), (5), (6), (6a), (6b) (7), (8), (9), (10), (11), (12), (13), (14), (A), (B), (C), (D), and so forth and so on," or a "compound" can include all or any sub-group of solvates, complexes, polymorphs, derivatives thereof (including but not limited to, radiolabeled derivatives (including deuterated derivatives where one or more H are replaced by D)), tautomers, stereoisomers, and optical isomers of the compound of the formulas listed herein and salts thereof.

As used herein, "control" can refer to an alternative subject or sample used in an experiment for comparison purposes and included to minimize or distinguish the effect of variables other than an independent variable. A control can be positive or negative.

As used herein, "concentrated" can refer to an amount of a molecule, compound, or composition, including, but not limited to, a chemical compound, polynucleotide, peptide, polypeptide, protein, antibody, or fragments thereof, that indicates that the sample is distinguishable from its naturally occurring counterpart in that the concentration or number of molecules per volume is greater than that of its naturally occurring counterpart.

As used herein, "derivative" can refer to a compound that is based off a lead compound described herein and can include all or any sub-group of solvates, complexes, polymorphs, derivatives thereof (including but not limited to, radiolabeled derivatives (including deuterated derivatives where one or more H are replaced by D)), tautomers, stereoisomers, and optical isomers of the compound of the formulas listed herein and salts thereof.

As used herein, "diluted" can refer to an amount of a molecule, compound, or composition including but not limited to, a chemical compound, polynucleotide, peptide, polypeptide, protein, antibody, or fragments thereof, that indicates that the sample is distinguishable from its naturally occurring counterpart in that the concentration or number of molecules per volume is less than that of its naturally occurring counterpart.

As used herein, "dose," "unit dose," or "dosage" can refer to physically discrete units suitable for use in a subject, each unit containing a predetermined quantity of a compound as provided herein and/or a pharmaceutical formulation thereof calculated to produce the desired response or responses in association with its administration.

As used herein, "effective amount" can refer to an amount sufficient to effect beneficial or desired results. An effective amount can be administered in one or more administrations, applications, or dosages. "Effective amount" can refer to an amount of a compound, derivative, and/or formulation thereof provided herein that can treat, prevent, and/or inhibit infection by *A. baumannii*. "Effective amount" can refer to an amount of a compound, derivative, and/or formulation thereof provided herein that can kill and/or inhibit the growth, amount, and/or pathogenicity of *A. baumannii*.

As used herein, "hydrate" can refer to a compound formed by the addition of water. Typically, but not always, this will be crystalline lattice structures that incorporate water molecules. Hydrates include stoichiometric hydrates, as well as compositions containing variable amounts of water.

As used herein, "mitigate" can refer to reducing a particular characteristic, symptom, or other biological or physiological parameter associated with a disease or disorder.

The term "molecular weight", as used herein, can generally refers to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

As used herein, "negative control" can refer to a "control" that is designed to produce no effect or result, provided that all reagents are functioning properly and that the experiment is properly conducted. Other terms that are interchangeable with "negative control" include "sham," "placebo," and "mock."

As used herein, "pharmaceutical formulation" can refer to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable" can refer to compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the Food and Drug Administration.

As used herein, "pharmaceutically acceptable carrier or excipient" can refer to a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used herein also includes both one and more than one such carrier or excipient. Pharmaceutically acceptable carriers include, but are not limited to, diluents, preservatives, binders, lubricants, disintegrators, swelling agents, fillers, stabilizers, and combinations thereof.

As used herein, "pharmaceutically acceptable salt" can refer to any salt derived from organic and inorganic acids of a compound described herein. Pharmaceutically acceptable salt also refers to a salt of a compound described having an acidic functional group, such as a carboxylic acid functional group, and a base. Pharmaceutically acceptable salt also includes hydrates of a salt of a compound described herein.

As used herein, "positive control" can refer to a "control" that is designed to produce the desired result, provided that all reagents are functioning properly and that the experiment is properly conducted.

As used herein, "preventative," "preventing," "prevent" and the like can refer to partially or completely delaying and/or precluding the onset or recurrence of a disorder or conditions and/or one or more of its attendant symptoms or barring a subject from acquiring or reacquiring a disorder or condition or reducing a subject's risk of acquiring or reacquiring a disorder or condition or one or more of its attendant symptoms including, but not limited to, malaria, infection and/or transmission of a parasite of the genus *Plasmodium* or a symptom thereof.

As used herein, "purified" or "purify" can be used in reference to a nucleic acid sequence, peptide, or polypeptide that has increased purity relative to the natural environment.

As used herein, "separated" can refer to the state of being physically divided from the original source or population such that the separated compound, agent, particle, chemical compound, or molecule can no longer be considered part of the original source or population.

As used herein, "solvate" refers to a complex of variable stoichiometry formed by a solute (e.g. formulas (1)-(1) (A), (B), (C), (D), or any other compound herein or a salt thereof) and a solvent. Pharmaceutically acceptable solvates may be formed for crystalline compounds wherein solvent molecules are incorporated into the crystalline lattice during crystallization. The incorporated solvent molecules can be water molecules or non-aqueous molecules, such as but not limited to, ethanol, isopropanol, dimethyl sulfoxide, acetic acid, ethanolamine, and ethyl acetate molecules.

As used interchangeably herein, "subject," "individual," or "patient," can refer to a vertebrate, preferably a mammal, more preferably a human. Mammals include, but are not limited to, murines, simians, humans, farm animals, sport animals, and pets. The term "pet" includes a dog, cat, guinea pig, mouse, rat, rabbit, ferret, and the like. The term farm animal includes a horse, sheep, goat, chicken, pig, cow, donkey, llama, alpaca, turkey, and the like.

As used herein, "substantially pure" can mean an object species is the predominant species present (i.e., on a molar basis it is more abundant than any other individual species in the composition), and preferably a substantially purified fraction is a composition wherein the object species comprises about 50 percent of all species present. Generally, a substantially pure composition will comprise more than about 80 percent of all species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single species.

The terms "sufficient" and "effective," as used interchangeably herein, can refer to an amount (e.g. mass, volume, dosage, concentration, and/or time period) needed to achieve one or more desired result(s). For example, a therapeutically effective amount refers to an amount needed to achieve one or more therapeutic effects.

As used herein, "synergistic effect," "synergism," or "synergy" can refer to an effect arising between two or more molecules, compounds, substances, factors, or compositions that that is greater than or different from the sum of their individual effects.

As used herein, "tangible medium of expression" can refer to a medium that is physically tangible and is not a mere abstract thought or an unrecorded spoken word. Tangible medium of expression includes, but is not limited to, words on a cellulosic or plastic material or data stored on a suitable device such as a flash memory or CD-ROM.

As used herein, "therapeutic", "treating", "treat," and the like can refer to include partially or completely delaying, alleviating, mitigating or reducing the intensity of one or more attendant symptoms of a disease or condition including, but not limited to, malaria, infection and/or transmission of a parasite of the genus *Plasmodium* or a symptom thereof.

As used herein, "alkyl" and "alkylene" refer to a saturated hydrocarbon chain having the specified number of member atoms.

The term "alkyl" can also refer to the radical of saturated aliphatic groups (i.e., an alkane with one hydrogen atom removed), including straight-chain alkyl groups, branched-chain alkyl groups, cycloalkyl (alicyclic) groups, alkyl-substituted cycloalkyl groups, and cycloalkyl-substituted alkyl groups. "Alkyl" also refers to a saturated hydrocarbon chain having the specified number of atoms.

The term "alkyl" (or "lower alkyl") as used herein can include both "unsubstituted alkyls" and "substituted alkyls," the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein can refer to an alkyl group, as defined above, but having from one to ten carbons in its backbone structure. Likewise, "lower alkenyl" and "lower alkynyl" have similar chain lengths.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Cycloalkyls can be substituted in the same manner.

As used herein, "$C_{1-6}$ alkyl" can refer to an alkyl group having any number of member atoms from 1 to 6 member atoms, such as for example 1 to 4 atoms. Other alkyl groups may have any number of member atoms as indicated by the numbers given in the formula, which, like the previous example, can refer to an alkyl group having any number of member atoms within the specified range of member atoms. Alkyl groups may be straight or branched. Representative branched alkyl groups have one, two, or three branches. Alkyl includes methyl, ethyl, propyl (n-propyl and isopropyl), butyl (n-butyl, isobutyl, and t-butyl), pentyl (n-pentyl, isopentyl, and neopentyl), and hexyl.

As used herein, "heterocyclic group" can refer to a non-aromatic ring and having the specified number of member atoms being saturated or having one or more degrees of unsaturation and, unless otherwise specified, containing one or more heteroatoms.

As used herein, "heteroaryl" can refer to an aromatic ring having the specified number of member atoms and, unless otherwise specified, containing one or more heteroatoms. Bicyclic and other polycyclic ring systems having a heteroaryl ring are described as fused systems.

The term "heteroalkyl," as used herein, can refer to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

The term "heteroalkyl," as used herein, can refer to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

As used herein, "alkoxyl" or "alkoxy," as used herein, can refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl is an ether or resembles an alkoxyl, such as can be represented by one of —O-alkyl, —O-alkenyl, and —O-alkynyl. The terms "aroxy" and "aryloxy", as used interchangeably herein, can be represented by —O-aryl or O-heteroaryl, wherein aryl and heteroaryl are as defined below. The alkoxy and aroxy groups can be substituted as described above for alkyl.

As used herein, "amine" and "amino" (and its protonated form) are art-recognized and refer to both unsubstituted and substituted amines, e.g., a moiety that can be represented by the general formula:

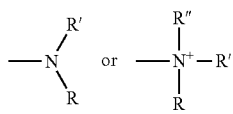

wherein R, R', and R" each independently represent a hydrogen, an alkyl, an alkenyl, —(CH2)$_m$—R$_C$ or R and R' taken together with the N atom to which they are attached complete a heterocycle having from 4 to 8 atoms in the ring structure; R$_C$ represents an aryl, a cycloalkyl, a cycloalkenyl, a heterocycle or a polycycle; and m is zero or an integer in the range of 1 to 8. In some embodiments, only one of R or R' can be a carbonyl, e.g., R, R' and the nitrogen together do not form an imide. In other embodiments, the term "amine" does not encompass amides, e.g., wherein one of R and R' represents a carbonyl. In further embodiments, R and R' (and optionally R") each independently represent a hydrogen, an alkyl or cycloakly, an alkenyl or cycloalkenyl, or alkynyl. Thus, the term "alkylamine" as used herein means an amine group, as defined above, having a substituted (as described above for alkyl) or unsubstituted alkyl attached thereto, i.e., at least one of R and R' is an alkyl group.

As used herein, "amido" is art-recognized as an amino-substituted carbonyl and includes a moiety that can be represented by the general formula:

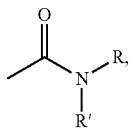

wherein R and R' are as defined above.

As used herein, "Aryl" can refer to C$_5$-C$_{10}$-membered aromatic, heterocyclic, fused aromatic, fused heterocyclic, biaromatic, or bihetereocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine, pyrimidine, and the like. Those aryl groups having heteroatoms in the ring structure may also be referred to as "aryl heterocycles" or "heteroaromatics." The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, and combinations thereof.

The term "aryl" can also include polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H, 6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. One or more of the rings can be substituted as defined above for "aryl."

As used herein, "aralkyl," can refer to an alkyl group substituted with an aryl group (e.g., an aromatic or heteroaromatic group).

As used herein, "aralkyloxy" can be represented by —O-aralkyl, wherein aralkyl is as defined above.

As used herein, "carbocycle," can refer to an aromatic or non-aromatic ring(s) in which each atom of the ring(s) is carbon.

As used herein, "heterocycle" or "heterocyclic" can refer to a monocyclic or bicyclic structure containing 3-10 ring atoms, and in some embodiments, containing from 5-6 ring atoms, wherein the ring atoms are carbon and one to four heteroatoms each selected from the following group of non-peroxide oxygen, sulfur, and N(Y) wherein Y is absent or is H, O, (C$_1$-C$_{10}$) alkyl, phenyl or benzyl, and optionally containing 1-3 double bonds and optionally substituted with one or more substituents. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. Heterocyclic groups can optionally be substituted with one or more substituents at one or more positions as defined above for alkyl and aryl, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbonyl" is art-recognized and includes such moieties as can be represented by the general formula:

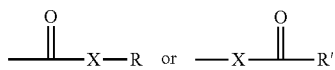

wherein X is a bond or represents an oxygen or a sulfur, and R and R' are as defined above. Where X is an oxygen and R or R' is not hydrogen, the formula represents an "ester". Where X is an oxygen and R is as defined above, the moiety is referred to herein as a carboxyl group, and particularly when R is a hydrogen, the formula represents a "carboxylic acid." Where X is an oxygen and R' is hydrogen, the formula represents a "formate." In general, where the oxygen atom of the above formula is replaced by sulfur, the formula represents a "thiocarbonyl" group. Where X is a sulfur and R or R' is not hydrogen, the formula represents a "thioester." Where X is a sulfur and R is hydrogen, the formula represents a "thiocarboxylic acid." Where X is a sulfur and R' is hydrogen, the formula represents a "thioformate." On the other hand, where X is a bond, and R is not hydrogen, the above formula represents a "ketone" group. Where X is a bond, and R is hydrogen, the above formula represents an "aldehyde" group.

As used herein, "heteroatom" as used herein can refer to an atom of any element other than carbon or hydrogen. Exemplary heteroatoms include, but are not limited to, boron, nitrogen, oxygen, phosphorus, sulfur, silicon, arsenic, and selenium.

As used herein, "nitro" can refer to —NO$_2$; the term "halogen" designates —F, —Cl, —Br, or —I; the term "sulfhydryl" refers to —SH; the term "hydroxyl" refers to —OH; and the term "sulfonyl" refers to —SO$_2$—.

The term "substituted" as used herein, can refer to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, e.g. 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, C$_3$-C$_{20}$ cyclic, substituted C$_3$-C$_{20}$ cyclic, heterocyclic, substituted heterocyclic, amino acid, peptide, and polypeptide groups.

Heteroatoms, such as nitrogen, can have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e., a compound that does not spontaneously undergo transformation such as by rearrangement, cyclization, elimination, etc.

As used herein, "suitable substituent" can refer to a chemically and pharmaceutically acceptable group, i.e., a moiety that does not significantly interfere with the preparation of or negate the efficacy of the inventive compounds. Such suitable substituents may be routinely chosen by those skilled in the art. Suitable substituents include but are not limited to the following: a halo, C$_1$-C$_6$ alkyl, C$_2$-C$_6$ alkenyl, C$_1$-C$_6$ haloalkyl, C$_1$-C$_6$ alkoxy, C$_1$-C$_6$ haloalkoxy, C$_2$-C$_6$ alkynyl, C$_3$-C$_8$ cycloalkenyl, (C$_3$-C$_8$ cycloalkyl)C$_1$-C$_6$ alkyl, (C$_3$-C$_8$ cycloalkyl)C$_2$-C$_6$ alkenyl, (C$_3$-C$_8$ cycloalkyl) C$_1$-C$_6$ alkoxy, C$_3$-C$_7$ heterocycloalkyl, (C$_3$-C$_7$ heterocycloalkyl) C$_1$-C$_6$ alkyl, (C$_3$-C$_7$ heterocycloalkyl)C$_2$-C$_6$ alkenyl, (C$_3$-C$_7$ heterocycloalkyl)C$_1$-C$_6$ alkoxy, hydroxy, carboxy, oxo, sulfanyl, C$_1$-C$_6$ alkylsulfanyl, aryl, heteroaryl, aryloxy, heteroaryloxy, arylalkyl, heteroaralkyl, arylalkoxy, heteroaralkoxy, nitro, cyano, amino, C$_1$-C$_6$ alkylamino, di-(C$_1$-C$_6$ alkyl)amino, carbamoyl, (C$_1$-C$_6$ alkyl)carbonyl, (C$_1$-C$_6$ alkoxy)carbonyl, (C$_1$-C$_6$ alkyl)aminocarbonyl, di-(C$_1$-C$_6$ alkyl)aminocarbonyl, arylcarbonyl, aryloxycarbonyl, (C$_1$-C$_6$ alkyl)sulfonyl, and arylsulfonyl. The groups listed above as suitable substituents are as defined hereinafter except that a suitable substituent may not be further optionally substituted.

As used herein, "optionally substituted" can indicate that a group may be unsubstituted or substituted with one or more substituents as defined herein.

Unless otherwise defined herein, all technical and scientific terms used herein have the same meaning as commonly understood by one of ordinary skill in the art.

Discussion

*Acinetobacter baumannii* is a successful nosocomial pathogens and causes infections that have become increasingly difficult to treat over the past few decades. The prolonged ability of *A. baumannii* to survive on abiotic surfaces combined with extensive antimicrobial resistance means that it not only survives but thrives in hospital settings. Consequently, there has been an alarming increase in mortality associated with infections caused by this difficult to treat organism. In addition to eliciting fatal nosocomial infections, this pathogen is a primary agent of infections in military personnel, often resulting from combat wounds or burns. These often result in chronic wound infections and biofilm-mediated disease, with the latter resulting from surgery and implanted devices. Such chronic *A. baumannii* infections lead to complications, extended rehabilitation, increased use of hospital resources, and considerably increased mortality.

Drug resistance in *A. baumannii* has resulted in few antibiotics left to eradicate the infections it causes, with clinicians often turning to last resort, toxic treatment options. The worldwide incidence of pan drug resistant (PDR) *A. baumannii* has spread quickly, at least in part due to its naturally transformable nature, leading to an increased capacity to acquire new determinants of resistance. PDR isolates are now resistant to all available antibiotics, including penicillins, cephalosporins, carbapenems, polymyxins, and tigecycline. The occurrence of PDR isolates, with no effective treatment options, seemingly marks the beginning of a post-antibiotic era for *A. baumannii*; thus, there is a need for the development of effective therapeutic options.

With that said, described herein are quinazoline-based compounds and formulations thereof. The compounds and formulations thereof can be antibacterial and can be effective to inhibit and/or kill *A. baumannii*. Also provided herein are methods of treating *A. baumannii* infection in a subject in need thereof by administering an amount, which can be an effective amount, of a quinazoline-based compound and formulation thereof as described herein. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Compounds and Pharmaceutical Formulations Thereof
Quinazoline-Based Compounds

Described herein are quinazoline-based compounds that can be effective at killing and/or inhibiting *A. baumannii*. The compound can have a structure according to Formula 1:

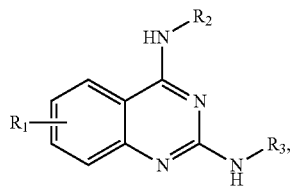

Formula 1 wherein $R_1$ can be selected from the group of:
6-Cl, 7-Cl, 6-Br, 7-Br, 6-Me, 7-Me, 6-OMe, 6-H, (6-H, 7-H),

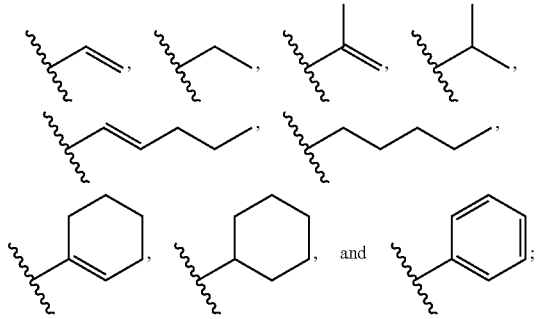

$R_2$ can be selected from the group of:
$CH_3$ and

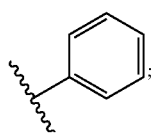 [SMILES: *c1ccccc1]

and $R_3$ can be selected from the group of:

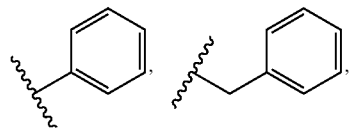

and $CH_3$.

In some embodiments, $R_1$ can be selected from the group of: 6-Br, 7-Br, 6-Me, 7-Me, (6-H, 7-H), 6-H, 6-Cl, and 6-OMe; $R_2$ can be $CH_3$; and $R_3$ can be

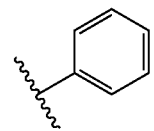 [SMILES: *c1ccccc1]

or

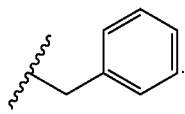

In some embodiments, $R_1$ can be selected from the group of: 6-Br, 6-Me, 7-Br, 7-Me, (6-H, 7-H); wherein $R_2$ can be $CH_3$; and $R_3$ can be

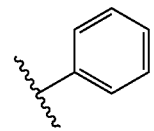 [SMILES: *c1ccccc1]

In some embodiments, $R_1$ can be selected from the group of: 6-H, 6-Cl, 6-OMe, 6-Br, and 6-Me; $R_2$ can be $CH_3$; and $R_3$ can be

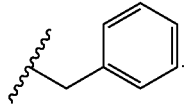

In some embodiments, $R_1$ can be selected from the group of: 6-Me,

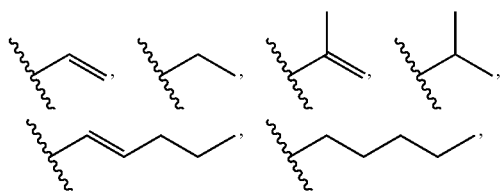

-continued

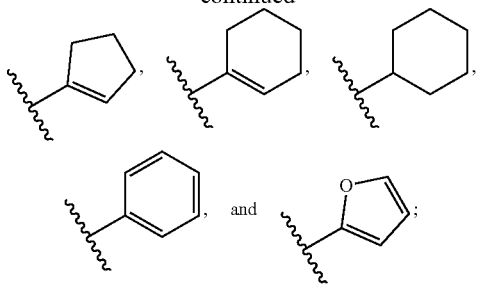

$R_2$ can be $CH_3$; and $R_3$ can be

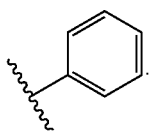 [SMILES: *c1ccccc1]

In some embodiments, $R_1$ can be selected from the group of: 6-Cl, 6-Br, 6-Me, 6-OMe, 7-Cl, 7-Br, and 7-Me; $R_2$ can be

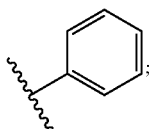 [SMILES: *c1ccccc1]

and $R_3$ can be $CH_3$.

In some embodiments, $R_1$ can be 6-Me; $R_2$ can be $CH_3$; and $R_3$ can be

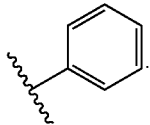 [SMILES: *c1ccccc1]

In some embodiments, $R_1$ can be 6-Br; $R_2$ can be $CH_3$; and $R_3$ can be

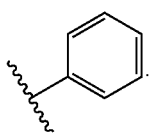

In some embodiments, $R_1$ can be 7-Me; $R_2$ can be $CH_3$; and $R_3$ can be

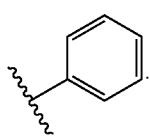 [SMILES: *c1ccccc1]

In some embodiments, $R_1$ can be

$R_2$ can be $CH_3$; and $R_3$ can be

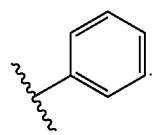

In some embodiments, $R_1$ can be

$R_2$ can be $CH_3$; and $R_3$ can be

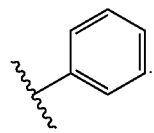

In some embodiments, $R_1$ can be

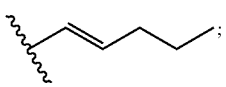 [SMILES: */C=C/CCC]

$R_2$ can be $CH_3$; and $R_3$ can be

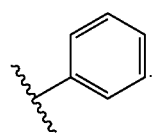

In some embodiments, $R_1$ can be

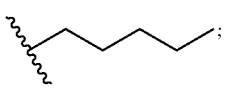

$R_2$ can be $CH_3$; and $R_3$ can be

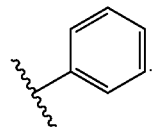

In some embodiments, $R_1$ can be

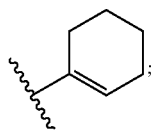 [SMILES: *C1=CCCCC1]

$R_2$ can be $CH_3$; and $R_3$ can be

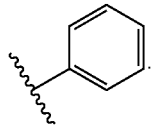 [SMILES: *c1ccccc1]

In some embodiments, $R_1$ can be

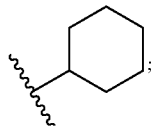

$R_2$ can be $CH_3$; and $R_3$ can be

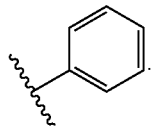 [SMILES: *c1ccccc1]

In some embodiments, $R_1$ can be

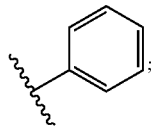

$R_2$ can be $CH_3$; and wherein $R_3$ can be

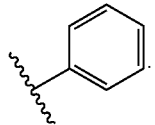 [SMILES: *c1ccccc1]

In some embodiments, the compound(s) can be effective to kill and/or inhibit at killing and/or inhibiting *A. baumannii*.

Pharmaceutical Formulations

The compounds (e.g. compounds having a structure according to Formula 1 or any other compound or formulas described herein) described herein can be provided to a subject in need thereof as an ingredient, such as an active ingredient, in a pharmaceutical formulation. As such, also described are pharmaceutical formulations containing one or more of the compounds and salts thereof, or pharmaceutically acceptable salts thereof described herein. Suitable salts include, but are not limited to, sulfate, citrate, acetate, oxalate, chloride, hydrochloride, bromide, hydrobromide, iodide, nitrate, bisulfate, phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, napthalenesulfonate, propionate, malonate, mandelate, malate, phthalate, and pamoate.

The pharmaceutical formulations or salts thereof can be administered to a subject in need thereof. In some embodiments, the subject is infected or suspected of being infected with or exposed to *A. baumannii*.

Pharmaceutically Acceptable Carriers and Auxiliary Ingredients and Agents The pharmaceutical formulations containing an effective amount of a compound described herein (e.g. compounds having a structure according to Formula 1 or any other formula or other formula described herein) or a derivative, such as a salt, thereof can further include a pharmaceutically acceptable carrier. Suitable pharmaceutically acceptable carriers include, but are not limited to water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxy methylcellulose, and polyvinyl pyrrolidone, which do not deleteriously react with the active composition.

The pharmaceutical formulations can be sterilized, and if desired, mixed with auxiliary agents, such as lubricants, preservatives, stabilizers, wetting agents, emulsifiers, salts for influencing osmotic pressure, buffers, coloring, flavoring and/or aromatic substances, and the like which do not deleteriously react with the active compound.

In addition to, an amount, such as an effective amount, of a compound and/or derivative (e.g. salt) thereof, the pharmaceutical formulations can also include an effective amount of auxiliary active agents, including but not limited to, antisense or RNA interference molecules, chemotherapeutics, or antineoplasic agents, hormones, antibiotics, antivirals, immunomodulating agents, antinausea, pain modifying compounds (such as opiates), anti-inflammatory agents, antipyretics, antibiotics, and/or antibodies or fragments thereof.

Effective Amounts of the Compounds, Derivatives Thereof, and Auxiliary Active Agents The effective amount of the compound (e.g. compounds having a structure according to Formula 1 or any other formula or other formula described herein) or a derivative, such as a salt, contained in the pharmaceutical formulation can range from about 0.001 micrograms to about 1000 grams. In some embodiments, the effective amount of the compound and/or derivative thereof can range from about 0.001 micrograms to about 0.01 micrograms. In other embodiments, the effective amount of compound and/or derivative thereof can range from about 0.01 micrograms to about 0.1 micrograms. In further embodiments, the effective amount of the compound and/or derivative thereof can range from about 0.1 micrograms to about 1.0 grams. In yet further embodiments, the effective amount of the compound and/or derivative thereof can range from about 1.0 grams to about 10 grams. In other embodiments, the effective amount of the compound and/or derivative thereof can range from about 10 grams to about 100 grams. In still other embodiments, the effective amount of the compound and/or derivative thereof can range from about 100 grams to about 1000 grams.

In embodiments where there is an auxiliary active agent contained in the compound or derivative thereof pharmaceutical formulation, the effective amount of the auxiliary active agent will vary depending on the auxiliary active agent. In some embodiments, the effective amount of the auxiliary active agent can range from 0.001 micrograms to about 1000 grams. In other embodiments, the effective amount of the auxiliary active agent can range from about 0.01 IU to about 1000 IU. In further embodiments, the effective amount of the auxiliary active agent can range from 0.001 mL to about 1000 mL. In yet other embodiments, the effective amount of the auxiliary active agent can range from about 1% w/w to about 50% w/w of the total pharmaceutical formulation. In additional embodiments, the effective amount of the auxiliary active agent can range from about 1% v/v to about 50% v/v of the total pharmaceutical formulation. In still other embodiments, the effective amount of the auxiliary active agent can range from about 1% w/v to about 50% w/v of the total pharmaceutical formulation.

The auxiliary active agent can be included in the pharmaceutical formulation or can exist as a stand-alone compound or pharmaceutical formulation that can be administered contemporaneously or sequentially with the compound, derivative thereof, or pharmaceutical formulation thereof. In embodiments where the auxiliary active agent is a stand-alone compound or pharmaceutical formulation, the effective amount of the auxiliary active agent can vary depending on the auxiliary active agent used. In some of these embodiments, the effective amount of the auxiliary active agent can range from 0.001 micrograms to about 1000 grams. In other embodiments, the effective amount of the auxiliary active agent can range from about 0.01 IU to about 1000 IU. In further embodiments, the effective amount of the auxiliary active agent can range from 0.001 mL to about 1000 mL. In yet other embodiments, the effective amount of the auxiliary active agent can range from about 1% w/w to about 50% w/w of the total auxiliary active agent pharmaceutical formulation. In additional embodiments, the effective amount of the auxiliary active agent can range from about 1% v/v to about 50% v/v of the total pharmaceutical formulation. In still other embodiments, the effective amount of the auxiliary active agent can range from about 1% w/v to about 50% w/v of the total auxiliary agent pharmaceutical formulation.

Dosage Forms

In some embodiments, the pharmaceutical formulations described herein can be in a dosage form. The dosage form can be administered to a subject in need thereof. In some embodiments, the subject in need thereof can be infected with, suspected to be infected with, and/or exposed to *A. baumannii*.

The dosage forms can be adapted for administration by any appropriate route. Appropriate routes include, but are not limited to, oral (including buccal or sublingual), rectal, intraocular, inhaled, intranasal, topical (including buccal, sublingual, or transdermal), vaginal, parenteral, subcutaneous, intramuscular, intravenous, internasal, and intradermal. Such formulations can be prepared by any method known in the art.

Dosage forms adapted for oral administration can discrete dosage units such as capsules, pellets or tablets, powders or granules, solutions, or suspensions in aqueous or non-aqueous liquids; edible foams or whips, or in oil-in-water liquid emulsions or water-in-oil liquid emulsions. In some embodiments, the pharmaceutical formulations adapted for oral administration also include one or more agents which flavor, preserve, color, or help disperse the pharmaceutical formulation. Dosage forms prepared for oral administration can also be in the form of a liquid solution that can be delivered as a foam, spray, or liquid solution. The oral dosage form can be administered to a subject in need thereof. In some embodiments, the subject in need thereof can be infected with, suspected to be infected with, and/or exposed to *A. baumannii.*

Where appropriate, the dosage forms described herein can be microencapsulated. The dosage form can also be prepared to prolong or sustain the release of any ingredient. In some embodiments, the compound or derivative thereof is the ingredient whose release is delayed. In other embodiments, the release of an auxiliary ingredient is delayed. Suitable methods for delaying the release of an ingredient include, but are not limited to, coating or embedding the ingredients in material in polymers, wax, gels, and the like. Delayed release dosage formulations can be prepared as described in standard references such as "Pharmaceutical dosage form tablets," eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on excipients, materials, equipment, and processes for preparing tablets and capsules and delayed release dosage forms of tablets and pellets, capsules, and granules. The delayed release can be anywhere from about an hour to about 3 months or more.

Examples of suitable coating materials include, but are not limited to, cellulose polymers such as cellulose acetate phthalate, hydroxypropyl cellulose, hydroxypropyl methylcellulose, hydroxypropyl methylcellulose phthalate, and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings may be formed with a different ratio of water soluble polymer, water insoluble polymers, and/or pH dependent polymers, with or without water insoluble/water soluble non polymeric excipient, to produce the desired release profile. The coating is either performed on the dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Where appropriate, the dosage forms described herein can be a liposome. In these embodiments, compound, derivative thereof, auxiliary active ingredient, and/or pharmaceutically acceptable salt thereof are incorporated into a liposome. In some embodiments, a compound, derivative thereof, auxiliary active ingredient, and/or pharmaceutically acceptable salts thereof is integrated into the lipid membrane of the liposome. In other embodiments, a compound, derivative thereof, auxiliary active ingredient, and/or pharmaceutically acceptable salt thereof are contained in the aqueous phase of the liposome. In embodiments where the dosage form is a liposome, the pharmaceutical formulation is thus a liposomal formulation. The liposomal formulation can be administered to a subject in need thereof. In some embodiments, the subject in need thereof can be infected with, suspected to be infected with, and/or exposed to *A. baumannii*.

Dosage forms adapted for topical administration can be formulated as ointments, creams, suspensions, lotions, powders, solutions, pastes, gels, sprays, aerosols, or oils. In some embodiments for treatments of the eye or other external tissues, for example the mouth or the skin, the pharmaceutical formulations are applied as a topical ointment or cream. When formulated in an ointment, the compound, derivative thereof, auxiliary active ingredient, and/or pharmaceutically acceptable salt thereof can be formulated with a paraffinic or water-miscible ointment base. In other embodiments, the active ingredient can be formulated in a cream with an oil-in-water cream base or a water-in-oil base. Dosage forms adapted for topical administration in the mouth include lozenges, pastilles, and mouth washes.

Dosage forms adapted for nasal or inhalation administration include aerosols, solutions, suspension drops, gels, or dry powders. In some embodiments, the compound, derivative thereof, auxiliary active ingredient, and/or pharmaceutically acceptable salt thereof in a dosage form adapted for inhalation is in a particle-size-reduced form that is obtained or obtainable by micronization. In some embodiments, the particle size of the size reduced (e.g. micronized) compound or salt or solvate thereof, is defined by a $D_{50}$ value of about 0.5 to about 10 microns as measured by an appropriate method known in the art. Dosage forms adapted for administration by inhalation also include particle dusts or mists. Suitable dosage forms wherein the carrier or excipient is a liquid for administration as a nasal spray or drops include aqueous or oil solutions/suspensions of an active ingredient, which may be generated by various types of metered dose pressurized aerosols, nebulizers, or insufflators. The nasal/inhalation formulations can be administered to a subject in need thereof. In some embodiments, the subject in need thereof can be infected with, suspected to be infected with, and/or exposed to *A. baumannii*.

In some embodiments, the dosage forms are aerosol formulations suitable for administration by inhalation. In some of these embodiments, the aerosol formulation contains a solution or fine suspension of a compound, derivative thereof, auxiliary active ingredient, and/or pharmaceutically acceptable salt thereof a pharmaceutically acceptable aqueous or non-aqueous solvent. Aerosol formulations can be presented in single or multi-dose quantities in sterile form in a sealed container. For some of these embodiments, the sealed container is a single dose or multi-dose nasal or an aerosol dispenser fitted with a metering valve (e.g. metered dose inhaler), which is intended for disposal once the contents of the container have been exhausted.

Where the aerosol dosage form is contained in an aerosol dispenser, the dispenser contains a suitable propellant under pressure, such as compressed air, carbon dioxide, or an organic propellant, including but not limited to a hydrofluorocarbon. The aerosol formulation dosage forms in other embodiments are contained in a pump-atomizer. The pressurized aerosol formulation can also contain a solution or a suspension of a compound, derivative thereof, auxiliary active ingredient, and/or pharmaceutically acceptable salt thereof. In further embodiments, the aerosol formulation also contains co-solvents and/or modifiers incorporated to improve, for example, the stability and/or taste and/or fine particle mass characteristics (amount and/or profile) of the formulation. Administration of the aerosol formulation can be once daily or several times daily, for example 2, 3, 4, or 8 times daily, in which 1, 2, or 3 doses are delivered each time. The aerosol formulations can be administered to a subject in need thereof. In some embodiments, the subject in need thereof can be infected with, suspected to be infected with, and/or exposed to *A. baumannii*.

For some dosage forms suitable and/or adapted for inhaled administration, the pharmaceutical formulation is a dry powder inhalable formulations. In addition to the compound, derivative thereof, auxiliary active ingredient, and/or pharmaceutically acceptable salt thereof, such a dosage form can contain a powder base such as lactose, glucose, trehalose, manitol, and/or starch. In some of these embodiments, the compound, derivative thereof, auxiliary active ingredient, and/or pharmaceutically acceptable salt thereof is in a particle-size reduced form. In further embodiments, a performance modifier, such as L-leucine or another amino acid, cellobiose octaacetate, and/or metals salts of stearic acid, such as magnesium or calcium stearate.

In some embodiments, the aerosol formulations are arranged so that each metered dose of aerosol contains a predetermined amount of an active ingredient, such as the one or more of the compounds described herein.

Dosage forms adapted for vaginal administration can be presented as pessaries, tampons, creams, gels, pastes, foams, or spray formulations. Dosage forms adapted for rectal administration include suppositories or enemas. The vaginal formulations can be administered to a subject in need thereof. In some embodiments, the subject in need thereof can be infected with, suspected to be infected with, and/or exposed to *A. baumannii*.

Dosage forms adapted for parenteral administration and/or adapted for injection can include aqueous and/or non-aqueous sterile injection solutions, which can contain antioxidants, buffers, bacteriostats, solutes that render the composition isotonic with the blood of the subject, and aqueous and non-aqueous sterile suspensions, which can include suspending agents and thickening agents. The dosage forms adapted for parenteral administration can be presented in a single-unit dose or multi-unit dose containers, including but not limited to sealed ampoules or vials. The doses can be lyophilized and re-suspended in a sterile carrier to reconstitute the dose prior to administration. Extemporaneous injection solutions and suspensions can be prepared in some embodiments, from sterile powders, granules, and tablets. The parenteral formulations can be administered to a subject in need thereof. In some embodiments, the subject in need thereof can be infected with, suspected to be infected with, and/or exposed to *A. baumannii*.

For some embodiments, the dosage form contains a predetermined amount of a compound and/or derivative thereof per unit dose. In an embodiment, the predetermined amount of the compound or derivative thereof is an effective amount of the compound and/or derivative thereof to treat, prevent, or mitigate one or more symptoms of infection with *A. baumannii*. In other embodiments, the predetermined amount of the compound and/or derivative thereof can be an appropriate fraction of the effective amount of the active ingredient. Such unit doses may therefore be administered once or more than once a day (e.g. 1, 2, 3, 4, 5, 6, or more times per day). Such pharmaceutical formulations may be prepared by any of the methods well known in the art.

In some embodiments, a compound described herein can be formulated as a spray, aerosol, foam, gel, other liquid form, powder or other solid form suitable for application to a surface. Such suitable forms and methods of making such forms will be appreciated by one of ordinary skill in the art. In some embodiments, the form suitable for application to a surface can be in a ready-to-use form that can be directly applied to a surface without, for example, additional preparation prior to use (e.g. dilution). In some embodiments, the compound described herein can be in a concentrated form that is diluted to an effective concentration or amount prior to use. In some embodiments, the formulation suitable to be applied to a surface can be effective to kill or inhibit *A. baumannii* that may be present on a surface to which the formulation or compound is applied.

Methods of Making the Compounds and Derivatives Thereof

The compounds (e.g. compounds having a structure according to Formula 1 or any other formula or compound provided herein) and derivatives, such as salts, thereof can be synthesized via many methods generally known to those of ordinary skill in the art and others as provided elsewhere herein. The present disclosure is not intended to be limited by the particular methods of synthesizing the compounds described herein. The skilled artisan will recognize additional methods of synthesizing the compounds described herein.

Methods of Using the Compounds and Formulations Thereof

Any amount of the compounds (e.g. compounds having a structure according to Formula 1 or any other formula or compound provided herein) and derivatives, such as salts, thereof, pharmaceutical formulations, and/or salts thereof described herein can be administered to a subject in need thereof one or more times per day, week, month, or year. In some embodiments, the amount administered is the effective amount of the compound, pharmaceutical formulation, and/or salt thereof. For example, the compounds, formulations, or salts thereof, can be administered in a daily dose. This amount may be given in a single dose per day. In other embodiments, the daily dose may be administered over multiple doses per day, in which each containing a fraction of the total daily dose to be administered (sub-doses). In some embodiments, the amount of doses delivered per day is 2, 3, 4, 5, or 6. In further embodiments, the compounds, formulations, or salts thereof are administered one or more times per week, such as 1, 2, 3, 4, 5, or 6 times per week. In other embodiments, the compounds, formulations, or salts thereof are administered one or more times per month, such as 1 to 5 times per month. In still further embodiments, the compounds, formulations, or salts thereof are administered one or more times per year, such as 1 to 11 times per year.

In some embodiments, the subject in need thereof can be infected with, suspected to be infected with, and/or exposed to *A. baumannii*.

In embodiments where more than one of compounds, formulations, additional therapeutic agents, salts thereof, or pharmaceutically acceptable salts thereof are administered to a subject in need thereof sequentially; the sequential administration may be close in time or remote in time. For example, administration of the second compound, formulation, or other therapeutic agent can occur within seconds or minutes (up to about 1 hour) after administration of the first agent (close in time). In other embodiments, administration of the second compound, formulation, or other therapeutic agent occurs at some other time that is more than an hour after administration of the first agent.

The amount of compounds, formulations, salts thereof (including pharmaceutically acceptable formulations and salts thereof) described herein can be administered in an amount ranging from about 0.001 mg to about 1000 mg per day, as calculated as the free or unsalted compound. In some embodiments the amount of the compound, formulation, or salt thereof (including pharmaceutically acceptable formulations and salts thereof) can range from 0.001 mg/kg bodyweight to 1000 mg/kg bodyweight. In some embodiments the amount is about 25, 50, or 100 mg/kg bodyweight. In some embodiments, the effective amount of the compound can range from 0.001 mg to about 1000 mg per day. In some embodiments, the effective amount of the compound can range from 5, 50, or 100 mg/kg bodyweight.

The compounds and formulations described herein can be administered in combinations with or include one or more other auxiliary agents. Suitable auxiliary agents include, but are not limited to antisense or RNA interference molecules, chemotherapeutics, anti-neoplasic agents, hormones, antibiotics, antivirals, immunomodulating agents, anti-nausea, pain modifying compounds (such as opiates), anti-inflammatory agents, antipyretics, antibiotics, and/or antibodies or fragments thereof. The compound(s), and/or formulation(s), and/or additional therapeutic agent(s) can be administered simultaneously or sequentially by any convenient route in separate or combined pharmaceutical formulations. The additional therapeutic agents can be provided in their optically pure form or a pharmaceutically acceptable salt thereof.

In some embodiments, the compounds and formulations thereof described herein can be administered or applied to a surface. The surface can be any solid surface. In some embodiments, the compounds and formulations thereof described herein can be used to kill and/or inhibit *A. baumannii* that can be present on the surface. In some embodiments, a compound and formulation thereof can be applied to the surface via a spray, aerosol, in a liquid form, in a solid form (e.g. a powder) or other suitable form. The compound and/or formulation thereof can be applied for an amount of time (e.g. a contact time). The contact time can range from about 15 seconds to 2 hours or more and any range or amount of time in between. In some embodiments, the compound or formulation thereof can be removed from the surface after the contact time.

Kits

The compounds (e.g. compounds having a structure according to formula 1 or any other compounds or formulas described herein), including derivatives, such as salts, thereof) and pharmaceutical formulations described herein can be presented as a combination kit. As used herein, the terms "combination kit" or "kit of parts" refers to the compounds, or pharmaceutical formulations and additional components that are used to package, sell, market, deliver, and/or administer the combination of elements or a single element, such as the active ingredient, contained therein. Such additional components include but are not limited to, packaging, syringes, blister packages, bottles, and the like. When one or more of the components (e.g. active agents) contained in the kit are administered simultaneously, the combination kit can contain the active agents in a single pharmaceutical formulation (e.g. a tablet) or in separate pharmaceutical formulations.

When the agents are not administered simultaneously, the combination kit can contain each agent in separate pharmaceutical formulations. The separate pharmaceutical formulations can be contained in a single package or in separate packages within the kit.

In some embodiments, the combination kit also includes instructions printed on or otherwise contained in a tangible medium of expression. The instructions can provide information regarding the content of the compound or pharmaceutical formulations contained therein, safety information regarding the content of the compound(s) or pharmaceutical formulation(s) contained therein, information regarding the dosages, indications for use, and/or recommended treatment regimen(s) for the compound(s) and/or pharmaceutical formulations contained therein. In some embodiments, the instructions provide directions for administering the compounds, pharmaceutical formulations, or salts thereof to a subject in need thereof. The subject in need thereof can be infected with, suspected to be infected with, and/or exposed to *A. baumannii*.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Introduction.

*Acinetobacter baumannii* is one of the most successful nosocomial pathogens, causing infections that have over the past few decades become increasingly difficult to treat. The prolonged ability of *A. baumannii* to survive on abiotic surfaces combined with extensive antimicrobial resistance means that it not only survives but thrives in hospital settings.[1] Consequently, there has been an alarming increase in mortality associated with infections caused by this difficult to treat organism.[2] In addition to eliciting fatal nosocomial infections, this pathogen is a primary agent of infections in military personnel, often resulting from combat wounds or burns.[3] These often result in chronic wound infections and biofilm-mediated disease, with the latter resulting from surgery and implanted devices.[3b] Such chronic *A. baumannii* infections lead to complications, extended rehabilitation, increased use of hospital resources, and considerably increased mortality.[3b]

Drug resistance in *A. baumannii* has resulted in few antibiotics left to eradicate the infections it causes, with clinicians often turning to last resort, toxic treatment options.[1, 4, 5] The worldwide incidence of pan drug resistant (PDR) *A. baumannii* has spread quickly, at least in part due to its naturally transformable nature, leading to an increased capacity to acquire new determinants of resistance.[1, 4] PDR isolates are now resistant to all available antibiotics, including penicillins, cephalosporins, carbapenems, polymyxins, and tigecycline.[4] The occurrence of PDR isolates, with no effective treatment options, seemingly marks the beginning of a post-antibiotic era for *A. baumannii*; thus, measures must be taken to identify effective therapeutic options.[6]

Quinazolines are an emerging class of compounds that have a broad range of biological activities ranging from anti-cancer, anti-inflammatory, anti-psychotic, anti-diabetic, anti-leishmanial,[7,8] and anti-bacterial.[9, 10, 11, 12, 13, 14] Kung et al. discovered a series of 2-substituted quinazolines with broad spectrum antibacterial activity, inhibiting RNA synthesis and translation in a broad range of bacterial species.[15] More relevant to this study, Harris et al. revealed 5-substituted 2,4-diaminoquinazolines that inhibited the dihydrofolate reductase (DHFR) enzyme of *Escherichia coli* and *S. aureus*.[16] In so doing, they determined that the 5-substituted position of the 2,4-diaminoquinazolines was not as important for enzyme binding affinity as the general structural type of the group. Unfortunately, these molecules were not specific towards the bacterial DHFR enzyme, but also inhibited the bovine liver DHFR enzyme.[16] Further analysis revealed that smaller substituents created greater activity in bacterial cells while larger substituents were more active towards the bovine enzyme. However, unlike the quinazolines identified in this study, the 5-substituted 2,4-diaminoquinazolines proved ineffective in animal models of infection.[16]

It has been recently shown the utility of $N^2,N^4$-disubstituted quinazoline-2,4-diamines for the treatment of *S. aureus* infections.[17] Specifically, we have shown them to be active against a library of MRSA isolates, displaying strong bactericidal activities, with limited cytotoxic and hemolytic capacities towards human cells. Mechanism of action profiling reveals that, much like other quinazoline compounds, they appear to function by targeting bacterial dihydrofolate reductase.[17, 18, 19, 20] See e.g. FIG. 1. It has also been shown their potential for anti-biofilm activity, low frequencies of mutation, and in vivo efficacy using murine models of peritonitis.[17]

In this Example, the impact of $N^2,N^4$-disubstituted quinazoline-2,4-diamines as antibacterial agents is further explored, focusing specifically on the Gram negative species *A. baumannii*. Using a library of multi-drug resistant isolates, we reveal that these compounds are broadly bactericidal dihydrofolate reductase inhibitors. In addition, it was observed that these compounds have low incidences of resistance and possess the potential for anti-biofilm activity. Finally, it was observed that the compounds are efficacious in vivo using a murine model of *A. baumannii* infection. As such, this Example can demonstrate for the very real potential of quinazoline derived compounds as antibacterial agents against the important human pathogen, *A. baumannii*.

Results

Synthetic Chemistry.

Synthesis of $N^2,N^4$-disubstituted quinazoline-2,4-diamines has been reported by us previously. The series of 6-aryl/vinyl/alkyl-$N^2$-benzyl-$N^4$-methylquinazolin-2,4-diamines were synthesized from $N^2$-benzyl-6-bromo-$N^4$-methylquinazolin-2,4-diamine using Suzuki-Miyaura coupling conditions followed by, in the case of the alkyl derivatives, hydrogenation of the vinyl compound with palladium on carbon (Scheme 1).[21]

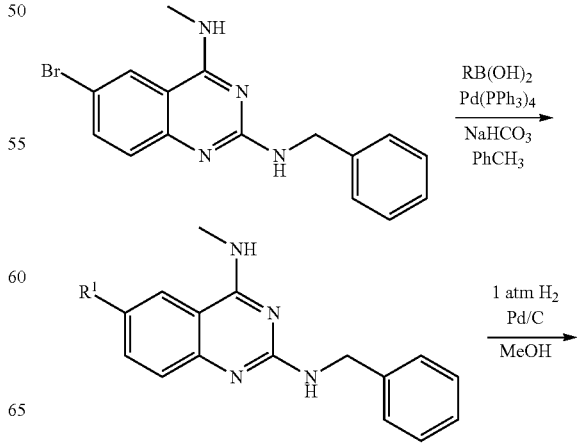

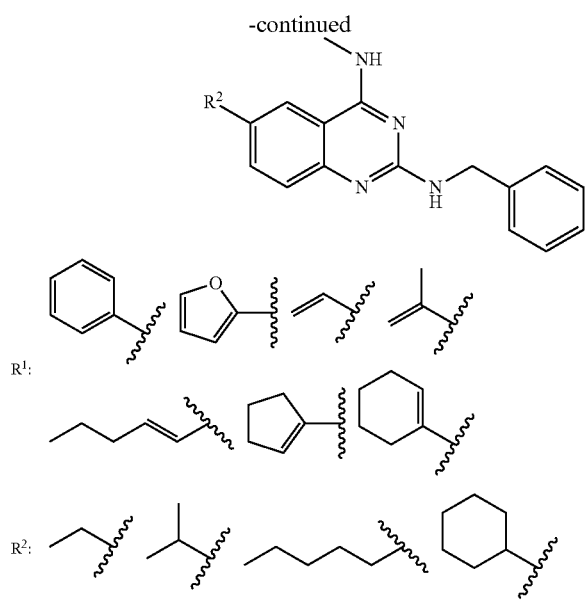

Structure-Activity Relationship Studies.

Our previously generated library of $N^2,N^4$-disubstituted quinazoline-2,4-diamines with reported activity against MRSA was screened against the other ESKAPE pathogens. In so doing, we identified a number of analogues that were effective against *A. baumannii*. To explore these findings more broadly, we expanded our studies to include a clonally diverse collection of *A. baumannii* isolates (Tables 1 and 7). Strong activity was found against a number of strains, with single digit micromolar MICs noted for three benzenoid substituted $N^2$-benzyl-$N^4$-methylquinazolin-2,4-diamines 1, 2, and 3 against the 1646 strain.

TABLE 1

SAR focusing on benzenoid ring substitution of various quinazoline-2,4-diamines[a]

| Compound | R | 1403 MIC (μM) | 1646 MIC (μM) | 1649 MIC (μM) | 1650 MIC (μM) | 1651 MIC (μM) | 1652 MIC (μM) |
|---|---|---|---|---|---|---|---|
| 1 | (6-Cl, HN-Me, NH-benzyl quinazoline-2,4-diamine) | 50 | 2 | 25 | 15 | 6 | 20 |
| 2 | (7-Cl, HN-Me, NH-benzyl quinazoline-2,4-diamine) | >50 | 6 | 30 | >50 | 10 | 50 |
| 3 | (6-OMe, HN-Me, NH-benzyl quinazoline-2,4-diamine) | >50 | 2 | 25 | 50 | 10 | 30 |

[a]Sulfamethoxazole (SMX) and trimethoprim (TMP) are internal controls for each in vitro MIC assay: SMX, 138 μM 1403, 118 μM 1646, 118 μM 1649, 118 μM 1650, 118 μM 1651, and 118 μM 1652; TMP, 103 μM 1403, 34 μM 1646, 517 μM 1649, 120 μM 1650, 103 μM 1651, and 103 μM 1652.

TABLE 7

*A. baumannii* strains used in this study. Strains used in this study are listed below along with their resistance profiles and provenance. The stains were chosen based on creating a screening panel of isolates with broad spectrum of resistance and clonal diversity.

| Strain ID | Identifying features | Provenance | References |
|---|---|---|---|
| 1403 | R = Ampicillin, Ciprofloaxacin, Gentamycin, Polymyxin B, Sulfamethoxazole, Trimethoprim, Sulfamethoxazole<br>S = Rifampin, Chloramphenicol, Tetracycline, Imepenem | Moffitt Cancer Center | Fleeman et al. (2015)[1] |
| 1646 | R = Sulfamethoxazole, Ciprofloaxacin, Ampicillin, Trimethoprim<br>S = Meropenem, Imipenem, Amikacin, Aztreonam, Amp-Sulbactam, Gentamycin, Piperacillin, Polymyxin B, Rifampin, Chloramphenicol, Cefepime, Cefotaxime, Ceftazidime, Ceftriaxone, Tetracycline, Tobramycin, | ATCC (1951) | Jacobs et al. (2010)[2] |
| 1649 | R = Ampicillin, Aztreonam, Cefotaxime, Sulfamethoxazole, Ceftriaxone, Tetracycline, Trimethoprim<br>S = Amikacin, Amp-Sulbactam, Cefepime, Gentamycin, Piperacillin, Timentin, Tobramycin, Levofloxacin, Polymyxin B, Rifampin, Ciprofloxacin, Chloramphenicol | CDC (TX, 1998) | Jacobs et al. (2010) |
| 1650 | R = Ampicillin, Aztreonam, Sulfamethoxazole, Tetracycline, Chloramphenicol, Trimethoprim<br>S = Amikacin, Amp-Sulbactam, Cefepime, Gentamycin, Piperacillin, Timentin, Tobramycin, Levofloxacin, Polymyxin B, Rifampin, Ciprofloxacin, Cefotaxime, Ceftriaxone | CDC (TX, 1998) | Jacobs et al. (2010) |
| 1651 | R = Ampicillin, Aztreonam, Sulfamethoxazole, Chloramphenicol, Trimethoprim<br>S = Amikacin, Amp-Sulbactam, Cefepime, Gentamycin, Piperacillin, Timentin, Tobramycin, Levofloxacin, Polymyxin B, Rifampin, Ciprofloxacin, Cefotaxime, Ceftriaxone, Tetracycline | CDC (TX, 1998) | Jacobs et al. (2010) |
| 1652 | R = Ampicillin, Aztreonam, Chloramphenicol, Sulfamethoxazole, Trimethoprim<br>S = Imipenem, meropenem, amikacin, Amp-Sulbactam, Levofloxacin, Cefepime, Cefotaxime, Ceftazidime, Ceftriaxone, Ciprofloxacin, Gentamicin, Piperacillin, Timentin, Tobramycin | CDC (TX, 1998) | Jacobs et al. (2010) |

Following the identification of active quinazolines 1, 2, and 3, additional $N^2$-benzyl-$N^4$-methylquinazolin-2,4-diamines were made with either 6- or 7-substitutions (Table 2). Substitution at the 6-position with a bromo or a methyl group was found to more beneficial for activity than substitution at the 7-position when comparing 6-bromo-quinazolin-2,4-diamine 4 with its 7-substituted counterpart 6 or the 6-methyl-substituted quinazoline 5 with its 7-substituted analogue 7. Importantly, $N^2$-benzyl-$N^4$-methylquinazolin-2,4-diamine analogue 8, which lacks any substitution at the benzenoid ring, was inactive with an MIC of ≥50 μM and therefore demonstrated the importance of a 6- or 7-substuent on the benzenoid ring.

TABLE 2

Probing benzenoid substitution of $N^2$-benzyl-$N^4$-methylquinazolin-2,4-diamines[a]

| Compound | R | 1403 MIC (μm) | 1646 MIC (μm) | 1649 MIC (μm) | 1650 MIC (μm) | 1651 MIC (μm) | 1652 MIC (μm) |
|---|---|---|---|---|---|---|---|
| 4 | 6-Br | 50 | 2 | 12 | 15 | 8 | 20 |
| 5 | 6-Me | 10 | 2 | 25 | 50 | 10 | 20 |

TABLE 2-continued

Probing benzenoid substitution of N²-benzyl-N⁴-methylquinazolin-2,4-diamines[a]

| Compound | R | 1403 MIC (μm) | 1646 MIC (μm) | 1649 MIC (μm) | 1650 MIC (μm) | 1651 MIC (μm) | 1652 MIC (μm) |
|---|---|---|---|---|---|---|---|
| 6 | 7-Br | >50 | 6 | 25 | >50 | 10 | >50 |
| 7 | 7-Me | 50 | 12 | 25 | 50 | 12 | 35 |
| 8 | 6-H, 7-H | >50 | 50 | >50 | >50 | >50 | >50 |

[a]Sulfamethoxazole (SMX) and trimethoprim (TMP) are internal controls for each in vitro MIC assay: SMX, 138 μM 1403, 118 μM 1646, 118 μM 1649, 118 μM 1650, 118 μM 1651, and 118 μM 1652; TMP, 103 μM 1403, 34 μM 1646, 517 μM 1649, 120 μM 1650, 103 μM 1651, and 103 μM 1652.

A similar trend was observed with N⁴-benzyl-N²-methylquinazolin-2,4-diamine analogues when comparing 6-substituted compounds 10 and 11 with the 7-substituted analogues 14 and 15 (Table 3). Furthermore, substitution in 6- or 7-position with an electron withdrawing chloro or a bromo moiety yielded quinazolines 9, 10, 13, or 14 which were more potent than corresponding methyl- or methoxy-substituted analogues 11, 12, or 15. Of all the quinazolines of the first two subseries tested, only compound 5 was active against the clinically important 1403 strain with an MIC of 10 μM, leading us to believe that continued work on the benzenoid ring would be highly beneficial.

(Table 4). Compound 16 with no benzenoid substitution was 4-fold more active than the benzyl analogue 8 (Table 1). Compounds 17-20 were also found to be slightly more active than the benzyl analogues 9-12 (Table 3) with MICs of 2 or 4 μM.

TABLE 3

Probing benzenoid ring substitution of N⁴-benzyl-N²-methylquinazolin-2,4-diamines[a]

| Compound | R | 1403 MIC (μM) | 1646 MIC (μM) | 1649 MIC (μM) | 1650 MIC (μM) | 1651 MIC (μM) | 1652 MIC (μM) |
|---|---|---|---|---|---|---|---|
| 9 | 6-Cl | >50 | 4 | 50 | 50 | 6 | >50 |
| 10 | 6-Br | >50 | 2 | 50 | >50 | >50 | >50 |
| 11 | 6-Me | >50 | 6 | >50 | >50 | 12 | >50 |
| 12 | 6-OMe | >50 | 6 | >50 | >50 | 8 | >50 |
| 13 | 7-Cl | >50 | 4 | >50 | >50 | >50 | >50 |
| 14 | 7-Br | >50 | 4 | >50 | >50 | >50 | >50 |
| 15 | 7-Me | >50 | 12 | >50 | >50 | >50 | >50 |

[a]Sulfamethoxazole (SMX) and trimethoprim (TMP) are internal controls for each in vitro MIC assay: SMX, 138 μM 1403, 118 μM 1646, 118 μM 1649, 118 μM 1650, 118 μM 1651, and 118 μM 1652; TMP, 103 μM 1403, 34 μM 1646, 517 μM 1649, 120 μM 1650, 103 μM 1651, and 103 μM 1652.

Extending the N²-benzyl chain to a N²-phenethyl was investigated to see if an increase in activity would be found

TABLE 4

Benzenoid ring substitutions of N⁴-methyl-N²-phenethylquinazolin-2,4-diamines[a]

| Compound | R | 1403 MIC (μM) | 1646 MIC (μM) | 1649 MIC (μM) | 1650 MIC (μM) | 1651 MIC (μM) | 1652 MIC (μM) |
|---|---|---|---|---|---|---|---|
| 16 | 6-H | >50 | 12 | >50 | >50 | >50 | >50 |
| 17 | 6-Cl | >50 | 2 | >50 | >50 | >50 | >50 |
| 18 | 6-OMe | >50 | 4 | >50 | >50 | >50 | >50 |
| 19 | 6-Br | >50 | 2 | >50 | >50 | 10 | >50 |
| 20 | 6-Me | >50 | 2 | >50 | >50 | 10 | >50 |

[a]Sulfamethoxazole (SMX) and trimethoprim (TMP) are internal controls for each in vitro MIC assay: SMX, 138 μM 1403, 118 μM 1646, 118 μM 1649, 118 μM 1650, 118 μM 1651, and 118 μM 1652; TMP, 103 μM 1403, 34 μM 1646, 517 μM 1649, 120 μM 1650, 103 μM 1651, and 103 μM 1652.

With the importance of substitution at the 6-position identified, new analogues were evaluated with vinyl, alkyl or aryl substitutions (Table 5). While the MIC barrier of 2 μM was not broken against the most susceptible strain (1646), major advances were seen in activity against the most resistant isolate (1403). In particular, n-pentyl-, cyclohexenyl- and cyclohexyl-substituted quinazolines 27, 29 and 30 had MICs of 2 μM against most isolates besides the 1652 strain for which they had MICs of 10 μM and 30 μM. These three compounds revealed that large, bulky and lipophilic groups at the 6-position are not only tolerated but beneficial for inhibiting the growth of *A. baumannii*. Phenyl- and furanyl-substituted quinazolines 31 and 32 were less active, as were the vinyl and ethyl analogues 22 and 23, the isopropenyl and isopropyl analogues 24 and 25, and the cyclopentenyl-quinazoline 28.

TABLE 5

Extension of the 6-position of N²-benzyl-N⁴-methylquinazolin-2,4-diamines[a]

| Compound | R | 1403 MIC (μM) | 1646 MIC (μM) | 1649 MIC (μM) | 1650 MIC (μM) | 1651 MIC (μM) | 1652 MIC (μM) |
|---|---|---|---|---|---|---|---|
| 21 | 6-Me | 10 | 2 | 25 | 50 | 10 | 20 |
| 22 | vinyl | 25 | 2 | 10 | 20 | 25 | 25 |
| 23 | ethyl | 30 | 2 | 10 | 30 | 2 | 30 |
| 24 | isopropenyl | >50 | 2 | 25 | >50 | 10 | >50 |
| 25 | isopropyl | >50 | 25 | 35 | >50 | 35 | >50 |
| 26 | pent-2-enyl | 10 | 2 | 10 | 25 | 2 | 30 |

TABLE 5-continued

Extension of the 6-position of $N^2$-benzyl-$N^4$-methylquinazolin-2,4-diamines[a]

| Compound | R | 1403 MIC (μM) | 1646 MIC (μM) | 1649 MIC (μM) | 1650 MIC (μM) | 1651 MIC (μM) | 1652 MIC (μM) |
|---|---|---|---|---|---|---|---|
| 27 | n-hexyl | 2 | 2 | 2 | 2 | 2 | 10 |
| 28 | cyclopentenyl | >50 | 2 | 50 | >50 | 30 | >50 |
| 29 | cyclohexenyl | 2 | 2 | 10 | 10 | 2 | 30 |
| 30 | cyclohexyl | 2 | 2 | 2 | 2 | 2 | 10 |
| 31 | phenyl | 30 | 10 | 20 | 20 | 2 | 50 |
| 32 | 2-furyl | 40 | 25 | >50 | >50 | 15 | >50 |

[a]Sulfamethoxazole (SMX) and trimethoprim (TMP) are internal controls for each in vitro MIC assay: SMX, 138 μM 1403, 118 μM 1646, 118 μM 1649, 118 μM 1650, 118 μM 1651, and 118 μM 1652; TMP, 103 μM 1403, 34 μM 1646, 517 μM 1649, 120 μM 1650, 103 μM 1651, and 103 μM 1652.

Testing for Bactericidal and Bacteriostatic Activity.

Lead quinazolines 4, 5, 26, 29, 27, and 30 were selected to be further evaluated for antimicrobial effects. The first assay utilized was a minimal bactericidal concentration (MBC) assay, to assess whether leads compounds were bacteriostatic or bactericidal. The six lead agents were screened to identify their $MBC_{90}$ towards each of the six $A.$ $baumannii$ isolates used in the SAR studies (Table 8), however for simplicity only the representative data for isolate 1646 is detailed below (Table 6). Lead agents were all found to be broadly bactericidal, with $MBC_{90}$ values ranging from 0.77 μM to 1.8 μM. Compounds 4 and 5 were found to be the most efficacious at eliminating bacterial growth, with $MBC_{90}$ values of 0.81 μM and 0.77 μM respectively. Further to this, we were able to obtain complete eradication of bacterial growth for these two compounds at 1 μM for 24 and 5 μM for 25. Although marginally less effective, compounds 26, 29, 30, and 27, all still efficiently reduced bacterial viability, with $MBC_{90}$ values of 1.8 μM, 1.5 μM, 1.1 μM, and 1.1 μM respectively. Moreover, compound 26 resulted in complete bacterial eradication at 5 μM, which is only 5× its MIC.

TABLE 6

In vitro antibacterial assessment of front runner quinazoline compounds against multi-drug resistant $A.$ $baumannii$.

| | Compound | | | | | |
|---|---|---|---|---|---|---|
| | 4 | 5 | 26 | 29 | 27 | 30 |
| MIC [μM] | 0.5 | 1 | 1 | 2 | 1 | 2 |
| $MBC_{90}$ [μM] | 0.8 | 0.8 | 1.8 | 1.5 | 1.1 | 1.1 |
| $MBEC_{90}$ [μM] | 3.3 | 2.8 | 8.9 | 8.9 | 11.5 | 41.2 |
| $LD_{50}$(HepG2) [μM] | 23 | 22 | 16 | 23 | 12 | 11 |
| AI | 46 | 22 | 22 | 12 | 12 | 6 |

TABLE 6-continued

In vitro antibacterial assessment of front runner quinazoline compounds against multi-drug resistant *A. baumannii*.

| Compound | | | | | |
|---|---|---|---|---|---|
| 4 | 5 | 26 | 29 | 27 | 30 |

TABLE 8

In vitro antibacterial assessment of front runner quinazoline compounds against a library of *A. baumannii* strains. Lead quinazolines were screened for MIC, $MBC_{90}$, and $MBEC_{90}$ against six *A. baumannii* strains (1403, 1646, 1649, 1650, 1651 and 1652). All data is in µM.

|  | 4 | 5 | 26 | 29 | 27 | 30 |
|---|---|---|---|---|---|---|
| MIC |  |  |  |  |  |  |
| 1403 | 25 | 10 | 10 | 3 | 15 | 20 |
| 1646 | 0.5 | 1 | 1 | 2 | 1 | 2 |
| 1649 | 11 | 21 | 10 | 8 | 10 | 15 |
| 1650 | 12 | 35 | 25 | 10 | 10 | 20 |
| 1651 | 5 | 1 | 2 | 2 | 10 | 20 |
| 1652 | 20 | 20 | 30 | 30 | 20 | 20 |
| $MBC_{90}$ |  |  |  |  |  |  |
| 1403 | 22 | 30 | 40 | 22 | 20 | 32 |
| 1646 | 0.81 | 0.77 | 1.8 | 1.5 | 1.1 | 1.1 |
| 1649 | 4.7 | 9.3 | 10 | 9.1 | 43 | 33 |
| 1650 | 15 | 27 | 16 | 16 | 20 | 22 |
| 1651 | 2.1 | 1.5 | 5.7 | 4.0 | 4.1 | 28 |
| 1652 | 9.7 | 12 | 23 | 11 | 23 | 17 |
| $MBEC_{90}$ |  |  |  |  |  |  |
| 1403 | 26 | 13 | 24 | 20 | 12 | 21 |
| 1646 | 3.3 | 2.8 | 8.9 | 8.9 | 12 | 41 |
| 1649 | 44.33 | 34 | 63 | 58 | 62 | 68 |
| 1650 | 9.61 | 21 | 50 | 48 | 49 | 46 |
| 1651 | 37.34 | 11 | 24 | 21 | 18 | 33 |
| 1652 | >100 | 68 | 97 | 77 | 64 | >100 |

Assessment of Biofilm Eradication Potential.

*A. baumannii*, like many nosocomial pathogens, utilizes biofilm formation to increase persistence and decrease sensitivity to the action of antibiotics. Accordingly, the ability to impact cell viability within a biofilm is an important attribute for novel antimicrobial compounds. As such, we next tested our isolates for this activity, again using our library of multi-drug resistant strains (Table 8), although as for the bactericidal data, only that from strain 1646 is discussed for ease of viewing. As with our bactericidal profiling, lead quinazolines 4 and 5 again had the most promising activity, with 90% biofilm eradication ($MBEC_{90}$) seen at 3.3 µM and 2.8 µM, respectively (Table 6). Further to this, analogue 5 was the most effective lead agent with a 3-log reduction in biofilm viability observed at 10 µM. Compound 4 reduced biofilm viability by 3.6-log, but not until a concentration of 50 µM. Lead quinazoline 30 had biofilm eradication potential similar to 4, reducing viability by 4.2-log at 50 µM, although its $MBEC_{90}$ (1 log reduction) was found to be close to this value at 41 µM. Compounds 26 and 29 also had promising activity with both displaying $MBEC_{90}$ at a concentration of 8.9 µM. Extended testing with these two quinazolines revealed that compound 29 reduced biofilm viability by 1.6-log at 50 µM, while 26 resulted in a 1.4-log reduction in biofilm viability at the same concentration.

Investigating the Mechanism of Action of the Quinazoline Derivatives.

To determine if the lead quinazolines inhibit the *A. baumannii* dihydrofolate reductase (DHFR) enzyme, similar to that seen for sister compounds in our work with MRSA, an in vitro rescue assay was performed.[17] Accordingly, the viability of *A. baumannii* cells was tested using lead quinazoline 5 in the presence or absence of tetrahydrofolic acid (THF, 0 µM-225 µM), the end product produced by DHFR. After 24 hours incubation, we determined that only 10 µM of THF was sufficient to rescue bacterial growth from the inhibitory effects of lead agent 25. This data confirms that these compounds exert their inhibitory effects on *A. baumannii* growth by blocking the activity of the essential DHFR enzyme.

Investigating the Potential for Resistance to Quinazolines.

Figure 2:
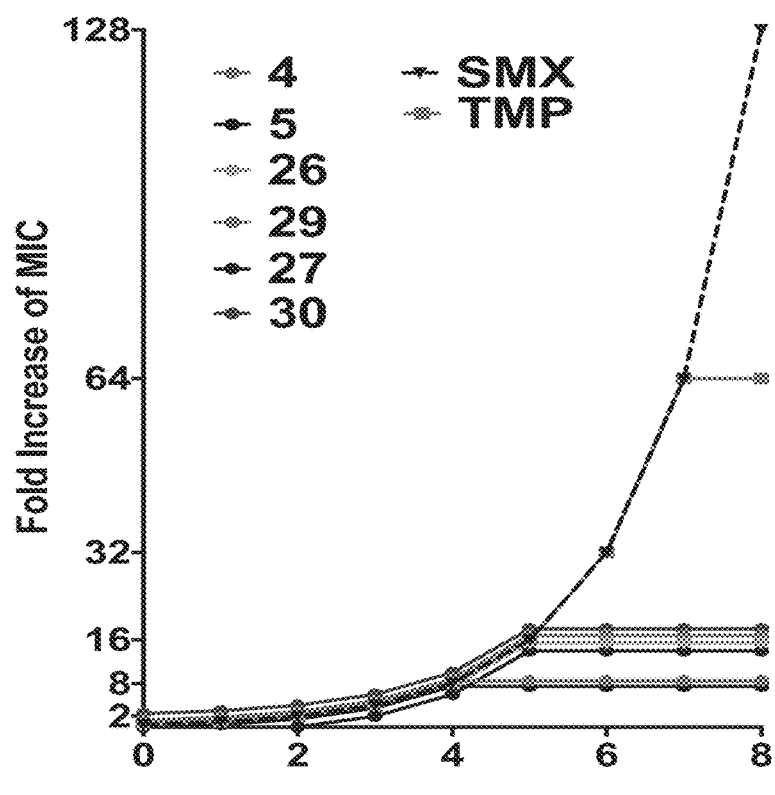
FIG. 2 shows a graph that can demonstrate that lead quinazolines generate limited resistance by *A. baumannii* isolates.

An important attribute of novel antibiotics is the ability to fend off the development of resistance towards their effects. To assess this capacity, *A. baumannii* strains were incubated overnight with 0.5× MIC of each of the frontrunners. The next day cells were washed and used to inoculate fresh media that contained a two-fold increase in drug. This was repeated for a total of 8 days, alongside sulfamethoxazole (SMX) and trimethoprim (TMP) controls, both of which target the same pathway as our lead agents (FIG. 2). Upon analysis, we determined that all of our frontrunner compounds out performed SMX and TMP, generating much lower incidences of resistance. Specifically, lead agents 4 and 5 had the most striking effects with MICs increasing over the 8-day test period by only 4-fold, compared to 64-fold (TMP) and 128-fold (SMX) for the control agents. Each of the other 4 agents were similarly impressive in their ability to limited resistance, resulting in an increased MIC of only 16-fold, which, whilst not as promising as 4 and 5, is still profoundly reduced compared to SMX and TMP.

Front Runner Quinazolines have Limited Toxicity Towards Human Cells.

Figure 4:
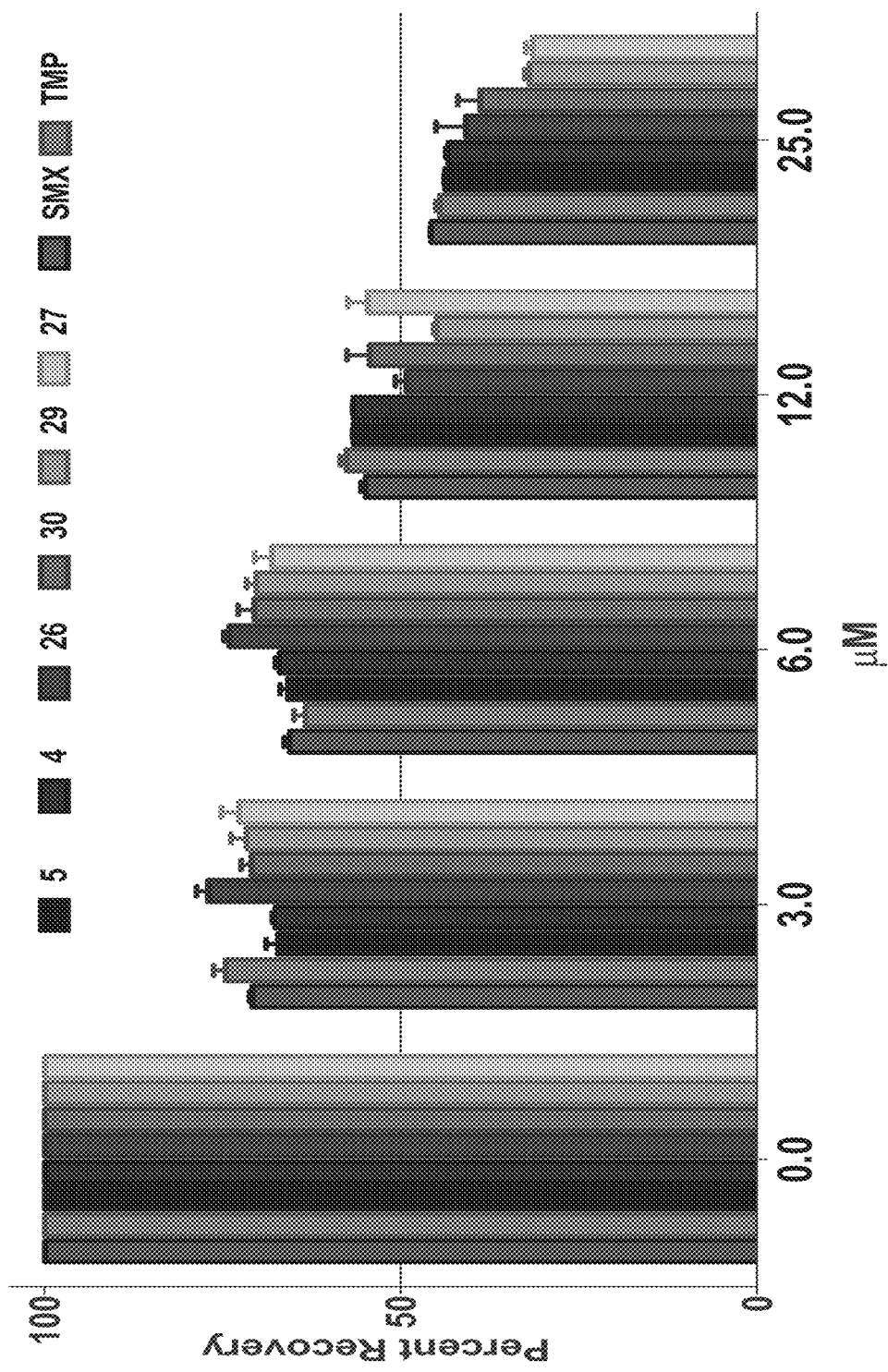
FIG. 4 shows a graph that demonstrates the results of lead quinazolines after testing at 25 μM, 12 μM, 6 μM, and 3 μM, against human HepG2 cells compared to solvent only controls. The known antibiotics sulfamethoxazole (SMX) and trimethoprim (TMP), which target the same pathway as our front runner agents, were also tested in parallel.
Figure 5:
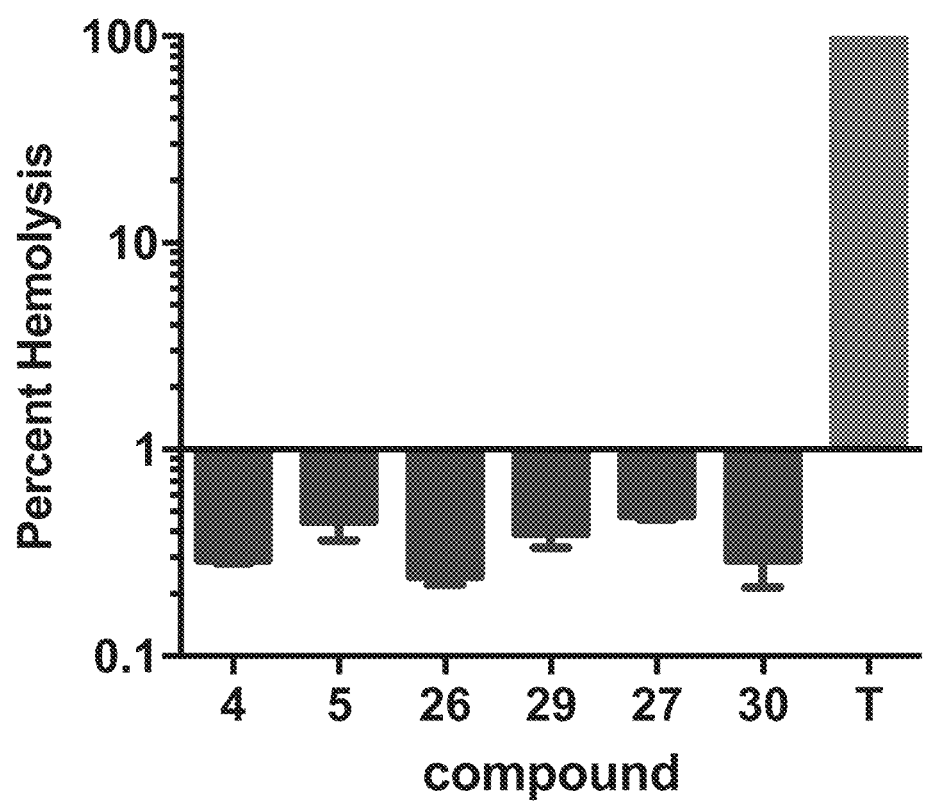
FIG. 5 shows a graph of demonstrating the hemolytic capabilities of lead quinazoline compounds. The six lead quinazolines were tested at about 10 μM against whole human blood for the ability to lyse erythrocytes. The graph depicts percent lysis of human red blood cells. Triton X-100 (T) was used as a positive control at a concentration of about 1%.

In order to gain a sense of the toxicity of lead quinazolines towards eukaryotic cells, we determined $LD_{50}$ values for human HepG2 cells (Table 6, FIG. 4). Importantly, we observed >50% cell viability for all compounds at concentrations up to 6 µM. Furthermore, 4 of our 6 leads returned >50% viability at 12 µM, whilst 26 and 29 were only marginally less promising, returning HepG2 cell viabilities of 49% and 42%, respectively, at this concentration. When treated with 25 µM of each lead quinazoline or control antibiotics we observed only fractionally less than 50% recovery. Importantly, lead agents 4 and 5 at 25 µM performed the best, with 43% and 44% viability observed, respectively. Similarly, lead agents 26 and 30 allowed for 41% and 39% respective viability at this concentration, while treatment with 27 and 29 resulted in 31% and 32% viability, respectively. The control compounds sulfamethoxazole and trimethoprim returned 46% and 45% viability at the highest concentration tested, which is in line with data generated from our front runners. To place lead compound data in context, it is apparent that 4 and 5 have the greatest therapeutic window for infection treatment. Specifically, lead agent 4 revealed a 46-fold difference in specificity towards bacteria, with an MIC (0.5 µM) much lower than the $LD_{50}$ towards human liver cells. Similarly, lead agent 5 displayed 22-fold specificity towards bacterial cells (Table 6). As an additional measure of toxicity, we next tested the hemolytic capacity of the front runners using whole human blood (FIG. 5). Importantly, we observed negligible capacity of our lead quinazolines to lyse human red blood cells when incubated for 1 hour at a concentration of 10 µM. Specifically, we observed average hemolysis well below 1%

(range=0.24%-0.47%), whilst the positive control (1% Triton X-100) produced 100% lysis during a similar time frame.

Murine Model of Lethal Peritonitis.

Figure 3:
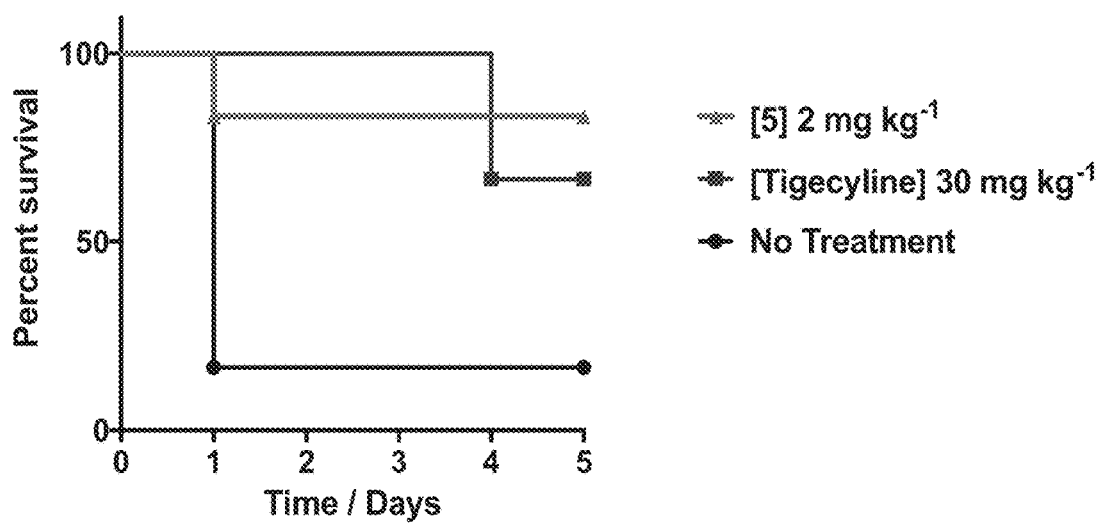
FIG. 3 shows a graph that can demonstrate that lead quinazolines are efficacious during a murine model of *A. baumannii* lethal peritonitis.

As a final assessment, we used a murine model of lethal *A. baumannii* infection to determine the efficacy of quinazolines in vivo. This was performed using frontrunner 5, which had the most promising properties from all of our biological testing. Accordingly, mice were inoculated with a lethal dose of *A. baumannii* via intraperitoneal injection on the right side of the abdomen. One hour post challenge, mice were treated with an intraperitoneal injection of 2 mg kg$^{-1}$ of frontrunner 5 on the left side of the abdomen. As a control, we also performed similar testing using 30 mg kg$^{-1}$ of tigecycline, which we already know our test strain to be susceptible to in vitro. In so doing, we determined that quinazoline 5 resulted in a statistically significant survival rate of 83% of infected animals, compared to only 17% for vehicle only controls (FIG. 3). We also saw significant survival of animals injected with tigecycline, although this was at a rate of 66%, which is inferior to that of our frontrunner agent. As such, this would suggest that our class of $N^2,N^4$-disubstitutedquinazoline-2,4-diamines have excellent potential for development as antibacterial agents targeting multi-drug resistant *A. baumannii* infections.

Summary.

A library of $N^2,N^4$-disubstituted quinazoline-2,4-diamines, which was previously shown to have antibacterial activity against MRSA,[17] was also found to have potent effects towards the multi-drug resistant Gram negative species *A. baumannii*. We assessed seventy-three $N^2,N^4$-disubstituted quinazoline-2,4-diamines and found that 6- or 7-substituted $N^2$-benzyl-$N^4$-methyl-quinazoline-2,4-diamines displayed promising activity, with MICs ranging from 0.5 to 30 μM against the six strains *A. baumannii* tested. Over thirty molecules were designed and synthesized to conduct a structure-activity relationship study to systematically probe the substituents in the $N^2$-, $N^4$-, 6-, and 7-positions. The most potent in vitro activities were obtained with quinazoline-2,4-diamines bearing a $N^2$-benzyl moiety and a $N^4$-methyl group. Furthermore, quinazolines substituted in 6-position with a halide or alkyl group were more potent compared to analogs substituted at the 7-position. 6-n-Pentyl- and 6-cyclohexyl-substituted quinazolines 27 and 30 were among the most effective agents since they were equipotent with single-digit μM MICs against the six tested *A. baumannii* strains. Following, frontrunner compounds 4, 5, 26, 29, 27, and 30 were tested for bactericidal activities and biofilm eradication. We found the lead quinazolines 4 and 5 displayed the strongest bactericidal and biofilm activity towards *A. baumannii*, with MBC$_{90}$ values <1 μM and MBEC$_{90}$ values <4 μM. These compounds also allowed for limited resistance development, displaying only a 4-fold increase in MIC against *A. baumannii* over an 8-day period, which was only a fraction of that observed for control compounds. Using a murine model of infection we determined that lead agent 5 was more effective, and at lower concentrations, in rescuing mice from a lethal dose of *A. baumannii* than our control agent Tigecycline. Our results reveal the potent antibacterial activities of $N^2$-benzyl-$N^4$-methyl-quinazoline-2,4-diamines against *A. baumannii*, and show their potential for development to treat both Gram-positive and Gram-negative multidrug resistant infections.

Methods.

General.

All commercially available chemical reagents, except for the boronic acids used, and anhydrous solvents were purchased from either Sigma Aldrich, Oakwood Products, Inc. or TCI America and used without any further purification. Boronic acids used were purchased through Frontier Scientific. NMR spectra were recorded at ambient temperature on a 400 MHz or 500 MHz Varian NMR spectrometer in the solvent indicated. All $^1$H NMR experiments are reported in δ units, parts per million (ppm) downfield of TMS, and were measured relative to the signals of chloroform (7.26 ppm) and dimethyl sulfoxide (39.5 ppm) with $^1$H decoupled observation. Data for $^1$H NMR are reported as follows: chemicals shift (δ ppm), multiplicity (s=singlet, d=doublet, t=triplet, q=quartet, p=pentet, m=multiplet), integration and coupling constant (Hz) whereas $^{13}$C NMR analyses were reported in terms of chemical shift. NMR data was analyzed by using MestReNova Software version 10.0.1-14719. The purity of the final compounds was determined to be ≥95')/o by high-performance liquid chromatography (HPLC) using an Agilent 1100 LC/MSD-VL with electrospray ionization. Low-resolution mass spectra were performed on an Agilent 1100 LC/MSD-VL with electrospray ionization. High resolution mass spectra (HRMS) were performed on an Agilent LC/MSD TOF system G3250AA. Analytical thin layer chromatography (TLC) was performed on silica gel 60 F254 precoated plates (0.25 mm) from EMD Chemical Inc., and components were visualized by ultraviolet light (254 nm). EMD silica gel 230-400 (particle size 40-63 μm) mesh was used for all flash column chromatography.

Synthetic Protocols and Compound Characterization

Procedure A:

Suzuki-Miyaura Cross Coupling with $N^2$-benzyl-$N^4$-methyl-6-bromo-quinazolin-2,4-diamine to yield $N^2$-benzyl-$N^4$-methyl-6-alken-yl-quinazlin-2,4-diamine and $N^2$-benzyl-M-methyl-6-aryl-quinazoline-2,4-diamine One equivalent of $N^2$-benzyl-$N^4$-methyl-6-bromo-quinazolin-2,4-diamine (0.23 mmol), 1.5 equivalents of the boronic acid (0.35 mmol), 5 mol-% of tetrakis-palladium, a saturated solution of sodium bicarbonate (1.23 mL), and anhydrous dimethoxyethane (1.87 mL) were combined in a sealed microwave tube, under argon, and heated in the microwave to 150° C. The reaction was monitored by TLC and LCMS until no starting material was observed. The reaction was cooled to room temperature, diluted with dichloromethane. The organic layer was separated and washed with equal volume of water three times, then dried over sodium sulfate. Purification of final product was completed by column chromatography using dichloromethane and methanol.

Procedure B: Hydrogenation of $N^2$-benzyl-M-methyl-6-alken-yl-quinazlin-2,4-diamine to Yield $N^2$-benzyl-M-methyl-6-alkan-yl-quinazoline-2,4-diamine One equivalent of $N^2$-benzyl-M-methyl-6-alken-yl-quinazlin-2,4-diamine was combined with 5 mol % of palladium on carbon in methanol to afford a 2 mg/mL solution and fixed with a hydrogen balloon. The reaction was monitored by LC-MS until no starting material was present. The reaction was filtered over celite and rinsed with three equal volumes of methanol. Purification by column chromatography using dichloromethane and methanol was used to obtain the pure product.

Procedure C: Cyclization of Anthranilic Acids to the Corresponding Quinazoline-2,4-diones One equivalent of the commercially available anthranilic acid and three equivalents of urea were ground in a mortar and pestle until a homogenous mixture was obtained. This powder was then transferred to a round bottom flask and heated to 200° C. uncovered. After 3 hours the mixture was cooled, triturated with 10 mL of water, the solid filtered and subsequently washed with 40 mL of water. Crude product was dried and no further purification was completed.

Procedure D: Chlorination of Quinazoline-2,4-diones to the Corresponding 2,4-Dichloroquinazoline One equivalent of quinazoline-2,4-dione and one equivalent of N,N-dimethylaniline were combined in a round bottom flask, 12 equivalents of phosphorus oxychloride was then added. The mixture was refluxed under argon until the presence of starting material was no longer seen by TLC or by LC-MS (6-24 hours). Upon completion the reaction mixture was cooled and slowly added to ice equaled to ten times that of the reaction volume. Upon precipitation the reaction was filtered and washed with water to afford the crude 2,4-dichloroquinazoline which was purified by column chromatography using hexanes and ethyl acetate.

Procedure E: Amine Substitution of 2,4-Dichloroquinzaolines to Yield 4-Amino-substituted-2-chloroquinazoline One equivalent of the crude 2,4-dichloroquinazoline, 1.1 equivalents of sodium acetate, and 1.1 equivalents were combined in a round bottom flask and mixed with a three to one solution of tetrahydrofuran and water to afford a 0.1 M solution. The reaction was heated to 65° C. and monitored until no starting material was seen by TLC or LC-MS. The reaction was diluted with ethyl acetate and the organic layer separated. This organic layer was washed three times with equal amounts of water and then dried over sodium sulfate. The crude 4-amino-substituted-2-chloroquinazoline was then purified by column chromatography using hexane and ethyl acetate.

Procedure F: Amine Substitution of 4-Aminosubstutited-2-chloroquinazolines to Yield 2,4-Diamino-substituted Quinazolines One equivalent of 4-aminosubstituted-2-chloroquinazoline and 1.5 equivalents of amine were combined with ethanol to create a 0.2 M solution which was heated to 150° C. in a sealed tube. The reaction was monitored by TLC and LC-MS for the absence of starting material (8-18 hours). The reaction was purified by either method $F^1$ or $F^2$.

Purification Method $F^1$:

Compound crystallized out of the cool solution, was filtered, and rinsed with cold ethanol.

Purification Method $F^2$:

Solvent was evaporated and crude product was purified via column chromatography using dichloromethane and methanol.

Compound 8 has been reported previously.[7]

2,6-Dichloro-N-methylquinazolin-4-amine 0.13 g (0.54 mmol) of 2,4,6-trichloroquinazoline was reacted with methylamine and purified according to general procedure C to furnish 0.11 g of the title compound in 92% yield. $^1$H NMR (500 MHz, CDCl$_3$) δ 7.69 (d, J=9.1 Hz, 1H), 7.37 (dd, J=9.1, 2.6 Hz, 1H), 6.97 (d, J=2.7 Hz, 1H), 3.86 (s, 3H), 3.22 (d, J=4.8 Hz, 3H). $^{13}$C NMR (126 MHz, CDCl$_3$) δ 161.2, 158.9, 151.5, 139.6, 126.9, 123.5, 122.2, 111.7, 28.6. R$_f$=0.82 (DCM/MeOH 10:1).

N$^2$-Benzyl-6-chloro-N$^4$-methylquinazoline-2,4-diamine (1)

0.10 g (0.44 mmol) of 2,6-dichloro-N-methylquinazolin-4-amine was reacted with benzylamine and purified according to general procedure D to furnish 87.0 mg of the title compound as a white crystalline solid in 45% yield. $^1$H NMR (400 MHz, CD$_3$OD) δ 7.80 (d, J=2.3 Hz, 1H), 7.41 (dd, J=8.9, 2.4 Hz, 1H), 7.34 (dd, J=7.9, 0.9 Hz, 2H), 7.29-7.22 (m, 3H), 7.20-7.13 (m, 1H), 4.63 (s, 2H), 2.98 (s, 3H). HRMS: m/z calculated for C$_{16}$H$_{16}$ClN$_4$ [M+H]$^+$ 299.1058; found 299.1061. R$_f$=0.33 (DCM/MeOH 10:1).

2,7-Dichloro-N-methylquinazolin-4-amine 0.20 g (0.86 mmol) of 2,4,7-trichloroquinazoline was reacted with methylamine and purified according to general procedure C to furnish 0.17 g of the title compound in 72% yield. $^1$H NMR (500 MHz, CDCl$_3$) δ 7.72 (d, J=2.0 Hz, 1H), 7.62 (d, J=8.8 Hz, 1H), 7.39 (dd, J=8.7, 2.0 Hz, 1H), 3.22 (d, J=4.9 Hz, 3H). $^{13}$C NMR (126 MHz, CDCl$_3$) δ 161.2, 158.9, 151.5, 139.6, 126.9, 122.2, 123.5, 111.7, 28.6. R$_f$=0.80 (DCM/MeOH 10:1).

N$^2$-Benzyl-7-chloro-N$^4$-methylquinazoline-2,4-diamine (2)

0.15 g (0.66 mmol) of 2,7-dichloro-N-methylquinazolin-4-amine was reacted with benzylamine and purified according to general procedure D to furnish 66.0 mg of the title compound as a white crystalline solid in 68% yield. $^1$H NMR (500 MHz, DMSO) δ 8.21-8.11 (m, 1H), 8.08 (d, J=8.5 Hz, 1H), 7.51 (d, J=7.8 Hz, 2H), 7.44 (t, J=7.8 Hz, 2H), 7.35 (q, J=7.5, 6.3 Hz, 2H), 7.18 (d, J=8.6 Hz, 1H), 4.70 (d, J=6.4 Hz, 2H), 3.53 (s, 1H), 3.09 (d, J=4.5 Hz, 3H). HRMS: m/z calculated for C$_{16}$H$_{16}$ClN$_4$ [M+H]+ 299.1058; found 299.1059. R$_f$=0.38 (DCM/MeOH 10:1).

2-Chloro-6-methoxy-N-methylquinazolin-4-amine 0.10 g (0.44 mmol) of 2,4-dichloro-6-methoxyquinazoline was reacted with methylamine and purified according to general procedure C to furnish 81 mg of the title compound in 83% yield. $^1$H NMR (500 MHz, CDCl$_3$) δ 8.12 (d, J=7.5 Hz, 1H), 7.56 (dd, J=7.5, 1.5 Hz, 1H), 6.78 (d, J=1.4 Hz, 1H), 3.87 (s, 2H), 2.91 (s, 2H), 2.30 (s, 1H). $^{13}$C NMR (126 MHz, CDCl$_3$) δ 160.7, 158.5, 154.2, 148.7, 127.3, 121.8, 110.5, 109.0, 55.8, 28.3. R$_f$=0.48 (DCM/MeOH 10:1).

N$^2$-Benzyl-6-methoxy-N$^4$-methylquinazoline-2,4-diamine (3)

70.0 mg (0.24 mmol) of 2-chloro-6-methoxy-N-methylquinazolin-4-amine was reacted with benzylamine and purified according to general procedure D to furnish 30.0 mg of the title compound as a white crystalline solid in 45% yield. $^1$H NMR (500 MHz, CDCl$_3$) δ 7.45 (d, J=9.1 Hz, 1H), 7.41 (d, J=7.1 Hz, 2H), 7.32 (t, J=7.6 Hz, 2H), 7.28-7.21 (m, 2H), 6.87 (d, J=2.7 Hz, 1H), 4.73 (d, J=5.7 Hz, 2H), 3.83 (s, 3H), 3.11 (d, J=4.7 Hz, 3H). HRMS: m/z calculated for C$_{17}$H$_{19}$N$_4$ [M+H]+ 295.1553; found 295.1556. R$_f$=0.26 (DCM/MeOH 10:1).

6-Bromo-2,4-dichloroquinazoline 3.0 g (13.89 mmol) of commercially available 2-amino-5-bromobenzoic acid was reacted according to general procedure C to give crude 6-bromoquinazoline-2,4(1H,3H)-dione. Without further purification, 3.4 g (14.12 mmol) of crude 6-bromoquinazoline-2,4(1H,3H)-dione was reacted and purified according to general procedure D to give 1.18 g of the title compound as a beige solid in 30% yield. $^1$H NMR (500 MHz, CDCl$_3$) δ 8.41 (d, J=2.1 Hz, 1H), 8.05 (dd, J=8.9, 2.1 Hz, 1H), 7.88 (d, J=8.9 Hz, 1H). $^{13}$C NMR (126

MHz, CDCl₃) δ 162.77, 155.44, 151.02, 139.71, 129.62, 128.21, 123.35, 123.21. R$_f$=0.88 (DCM/MeOH 10:1).

6-Bromo-2-chloro-N-methylquinazolin-4-amine 100 mg (0.36 mmol) of 6-bromo-2,4-dichloroquinazoline was reacted with methylamine and purified according to procedure E to furnish 89 mg of the title compound in 91% yield. $^1$H NMR (500 MHz, CDCl₃) δ 7.82 (d, J=1.9 Hz, 1H), 7.79 (dd, J=8.8, 2.0 Hz, 1H), 7.64 (d, J=8.8 Hz, 1H), 5.98 (s, 1H), 3.22 (d, J=4.9 Hz, 3H). $^{13}$C NMR (126 MHz, CDCl) δ 160.48, 158.07, 149.43, 136.75, 129.62, 123.44, 119.29, 114.59, 28.67. R$_f$=0.54 (DCM/MeOH 10:1).

N²-Benzyl-6-bromo-N⁴-methylquinazoline-2,4-diamine (4)

80 mg (0.29 mmol) of 6-bromo-2-chloro-N-methylquinazolin-4-amine was reacted with benzylamine and purified according to method F² to furnish 78 mg of the title compound as a white crystalline solid in 78% yield. $^1$H NMR (500 MHz, DMSO) δ 8.27 (s, 1H), 8.10 (s, 1H), 7.64 (d, J=8.9 Hz, 1H), 7.44 (d, J=7.6 Hz, 2H), 7.37 (t, J=7.5 Hz, 2H), 7.27 (dd, J=14.6, 7.7 Hz, 2H), 4.64 (d, J=6.3 Hz, 2H), 3.47 (d, J=4.2 Hz, 1H), 3.02 (d, J=3.1 Hz, 3H). HRMS: m/z calculated for C₁₆H₁₆BrN₄ [M+H]⁺ 343.0553; found 343.0544. R$_f$=0.51 (DCM/MeOH 10:1).

2,4-Dichloro-6-methylquinazoline 1.5 g (9.93 mmol) of commercially available 2-Amino-5-methylbenzoic acid was reacted according to general procedure C to give crude 6-methylquinazoline-2,4(1H,3H)-dione. Without further purification, 1.6 g (9.52 mmol) of crude 6-methylquinazoline-2,4(1H,3H)-dione was reacted and purified according to general procedure D to give 465 mg of the title compound as a beige solid in 23% yield. $^1$H NMR (500 MHz, CDCl₃) δ 8.00 (s, 2H), 7.88 (d, J=8.6 Hz, 2H), 7.81 (dd, J=8.6, 1.8 Hz, 2H), 2.60 (s, 7H). $^{13}$C NMR (126 MHz, CDCl₃) δ 163.07, 154.19, 150.96, 139.97, 138.37, 127.64, 124.66, 122.24, 21.88.

2-Chloro-N,6-dimethylquinazolin-4-amine 150 mg (0.70 mmol) of 2,4-dichloro-6-methylquinazoline was reacted with methylamine and purified according to procedure E to furnish 95 mg of the title compound in 66% yield. $^1$H NMR (500 MHz, CDCl₃) δ 7.63 (d, J=8.5 Hz, 1H), 7.53 (dd, J=8.5, 1.1 Hz, 1H), 7.45 (s, 1H), 6.13 (s, 1H), 3.20 (d, J=4.9 Hz, 3H), 2.45 (s, 3H). $^{13}$C NMR (126 MHz, CDCl₃) δ 161.24, 156.96, 148.85, 136.28, 135.23, 127.42, 120.03, 113.20, 28.51, 21.61. R$_f$=0.44 (DCM/MeOH 10:1).

N²-Benzyl-N⁴,6-dimethylquinazoline-2,4-diamine (5)

80 mg (0.38 mmol) of 2-chloro-N,6-dimethylquinazolin-4-amine was reacted with benzylamine and purified according to method F¹ to furnish 47 mg of the title compound as a beige crystalline solid in 57% yield. $^1$H NMR (500 MHz, CDCl₃) δ 7.45-7.23 (m, 8H), 5.85 (s, 1H), 5.41 (s, 1H), 4.75 (d, J=5.4 Hz, 2H), 3.10 (d, J=4.8 Hz, 3H), 2.39 (s, 3H). HRMS: m/z calculated for C₁₇H₁₉N₄ [M+H]⁺ 279.1604; found 279.1607. R$_f$=0.55 (DCM/MeOH 10:1).

7-Bromo-2,4-dichloroquinazoline 5.0 g (23.15 mmol) of commercially available 2-Amino-6-bromobenzoic acid was reacted according to general procedure C to give crude 7-bromoquinazoline-2,4(1H,3H)-dione. Without further purification, 5.2 g (21.58 mmol) of crude 7-bromoquinazoline-2,4(1H,3H)-dione was reacted and purified according to general procedure D to give 2.82 g of the title compound as a beige solid in 47% yield. $^1$H NMR (500 MHz, CDCl₃) δ 8.19 (d, J=1.6 Hz, 1H), 8.12 (d, J=8.9 Hz, 1H), 7.83 (dd, J=8.9, 1.8 Hz, 1H). $^{13}$C NMR (126 MHz, CDCl₃) δ 164.02, 156.23, 152.76, 133.01, 131.61, 130.47, 127.20, 121.10. R$_f$=0.90 (DCM/MeOH 10:1).

7-Bromo-2-chloro-N-methylquinazolin-4-amine 100 mg (0.36 mmol) of 7-bromo-2,4-dichloroquinazoline was reacted with methylamine and purified according to procedure E to furnish 95 mg of the title compound in 97% yield. $^1$H NMR (500 MHz, CDCl₃) δ 7.93 (d, J=1.7 Hz, 2H), 7.53 (dt, J=18.2, 5.3 Hz, 5H), 5.97 (s, 2H), 3.22 (d, J=4.9 Hz, 7H). $^{13}$C NMR (126 MHz, CDCl₃) δ 161.31, 158.76, 151.61, 130.40, 129.59, 127.99, 121.95, 112.01, 28.64. R$_f$=0.35 (DCM/MeOH 10:1).

N²-Benzyl-7-bromo-N⁴-methylquinazoline-2,4-diamine (6)

90 mg (0.33 mmol) of 7-bromo-2-chloro-N-methylquinazolin-4-amine was reacted with benzylamine and purified according to method F² to furnish 58 mg of the title compound as a white crystalline solid in 51% yield. $^1$H NMR (500 MHz, Methanol-d₄) δ 7.69 (d, J=8.7 Hz, 1H), 7.49 (s, 1H), 7.39-7.36 (m, 2H), 7.30 (t, J=7.7 Hz, 2H), 7.23-7.20 (m, 1H), 7.19 (dd, J=8.7, 2.0 Hz, 1H), 4.66 (s, 2H), 3.02 (s, 3H). HRMS: m/z calculated for C₁₆H₁₆BrN₄ [M+H]⁺ 343.0553; found 343.0548. R$_f$=0.59 (DCM/MeOH 10:1).

2,4-Dichloro-7-methylquinazoline 2.38 g (15.75 mmol) of commercially available 2-Amino-6-methylbenzoic acid was reacted according to general procedure C to give crude 7-methylquinazoline-2,4(1H,3H)-dione. Without further purification, 2.8 g (16.37 mmol) of crude 7-methylquinazoline-2,4(1H,3H)-dione was reacted and purified according to general procedure D to give 1.2 g of the title compound as a beige solid in 34% yield. $^1$H NMR (500 MHz, CDCl₃) δ 7.58 (d, J=8.4 Hz, 1H), 7.50 (s, 1H), 7.26-7.22 (m, 1H), 6.20 (s, 1H), 3.19 (d, J=4.9 Hz, 3H), 2.47 (s, 3H). $^{13}$C NMR (126 MHz, CDCl₃) δ 161.47, 157.79, 150.81, 144.35, 128.04, 126.97, 120.59, 111.22, 28.46, 21.85.

2-Chloro-N,7-dimethylquinazolin-4-amine 150 mg (0.70 mmol) of 2,4-dichloro-7-methylquinazoline was reacted with methylamine and purified according to procedure E to furnish 125 mg of the title compound in 86% yield $^1$H NMR (500 MHz, CDCl₃) δ 8.12 (d, J=8.6 Hz, 2H), 7.75 (s, 2H), 7.55 (dd, J=8.6, 1.3 Hz, 2H), 2.61 (s, 7H). $^{13}$C NMR (126 MHz, CDCl₃) δ 163.40, 155.13, 152.64, 147.95, 131.44, 126.93, 125.65, 120.46, 22.32. R$_f$=0.38 (DCM/MeOH 10:1).

N²-Benzyl-N⁴,7-dimethylquinazoline-2,4-diamine (7)

110 mg (0.53 mmol) of 2-chloro-N,7-dimethylquinazolin-4-amine was reacted with benzylamine and purified according to method F¹ to furnish 129 mg of the title compound as a beige crystalline solid in 88% yield. $^1$H NMR (500 MHz, CDCl$_3$) δ 7.60 (d, J=8.4 Hz, 1H), 7.51 (s, 1H), 7.25 (dd, J=8.4, 1.7 Hz, 1H), 4.80 (s, 2H), 3.20 (d, J=4.8 Hz, 3H), 2.48 (s, 3H). HRMS: m/z calculated for C$_{17}$H$_{19}$N$_4$ [M+H]$^+$ 279.1604; found 279.1598. R$_f$=0.49 (DCM/MeOH 10:1).

N$^4$-Benzyl-6-chloro-N$^2$-methylquinazoline-2,4-diamine (9)

80.0 mg (0.26 mmol) of N-benzyl-2,6-dichloroquinazolin-4-amine was reacted with methylamine and purified according to general procedure F to furnish 72.0 mg of the title compound as a beige crystalline solid in 67% yield. $^1$H NMR (500 MHz, CDCl$_3$) δ 7.49-7.36 (m, 7H), 7.34 (dd, J=5.8, 2.7 Hz, 1H), 4.79 (s, 2H), 3.06 (s, 3H). $^{13}$C NMR (126 MHz, CDCl$_3$) δ 160.3, 159.0, 150.8, 138.3, 133.1, 129.0, 128.8, 128.0, 127.7, 127.3, 125.7, 120.2, 45.2, 28.4. HRMS: m/z calculated for C$_{16}$H$_{16}$ClN$_4$ [M+H]+ 299.1058; found 299.1058. R$_f$=0.28 (DCM/MeOH 10:1).

N-Benzyl-6-bromo-2-chloroquinazolin-4-amine 0.10 g (0.36 mmol) of 6-bromo-2,4-dichloroquinazoline was reacted with benzylamine and purified according to general procedure E to furnish 0.13 g of the title compound in 99% yield. $^1$H NMR (500 MHz, CDCl$_3$) δ 7.84-7.79 (m, 2H), 7.67 (d, J=8.8 Hz, 1H), 7.44-7.36 (m, 5H), 6.01 (s, br, 1H), 4.86 (d, J=5.3 Hz, 2H). $^{13}$C NMR (126 MHz, CDCl$_3$) δ 159.6, 158.0, 149.7, 138.3, 136.9, 129.7, 129.0, 128.4, 128.3, 123.4, 119.4, 114.4, 46.0. R$_f$=0.60 (DCM/MeOH 10:1).

N$^4$-Benzyl-6-bromo-N$^2$-methylquinazoline-2,4-diamine (10)

0.12 g (0.34 mmol) N-benzyl-6-bromo-2-chloroquinazolin-4-amine was reacted with methylamine and purified according to general procedure F to furnish 92.0 mg of the title compound as a beige crystalline solid in 88% yield. $^1$H NMR (500 MHz, DMSO) δ 8.65 (s, br, 1H), 8.48 (s, 1H), 7.75 (d, J=8.9, 1H), 7.55-7.40 (m, 5H), 6.81 (s, br, 1H), 4.88 (d, J=5.8 Hz, 2H), 2.98 (t, J=3.6 Hz, 3H). HRMS: m/z calculated for C$_{16}$H$_{16}$BrN$_4$ [M+H]+ 343.0553; found 343.0549. R$_f$=0.52 (DCM/MeOH 10:1). N-Benzyl-2-chloro-6-methylquinazolin-4-amine: 0.10 g (0.47 mmol) of 2,4-dichloro-6-methylquinazoline was reacted with benzylamine and purified according to general procedure E to furnish 0.13 g of the title compound in 86% yield. $^1$H NMR (500 MHz, CDCl$_3$) δ 7.68 (s, 1H), 7.56 (d, J=8.4 Hz, 1H), 7.45-7.32 (m, 6H), 6.05 (s, br, 1H), 4.86 (s, 2H), 2.47 (s, 3H). $^{13}$C NMR (126 MHz, CDCl$_3$) δ 160.3, 156.9, 149.2, 137.4, 136.39, 135.4, 131.8, 128.9, 128.4, 127.6, 119.9, 113.0, 45.7, 21.6. R$_f$=0.61 (DCM/MeOH 10:1).

N$^4$-Benzyl-N$^2$,6-dimethylquinazoline-2,4-diamine (11)

0.11 g (0.41 mmol) N-benzyl-2-chloro-6-methylquinazolin-4-amine was reacted with methylamine and purified according to general procedure F to furnish 92.0 mg of the title compound as a beige crystalline solid in 81% yield. $^1$H NMR (500 MHz, CDCl$_3$) δ 7.39-7.28 (m, 8H), 4.81 (d, J=5.4 Hz, 2H), 3.05 (d, J=5.1 Hz, 3H), 2.37 (s, 3H). HRMS: m/z calculated for C$_{17}$H$_{19}$N$_4$ [M+H]+ 279.1604; found 279.1595. R$_f$=0.55 (DCM/MeOH 10:1).

N-Benzyl-2-chloro-6-methoxyquinazolin-4-amine 0.10 g (0.51 mmol) of 2,4-dichloro-6-methoxyquinazoline was reacted with benzylamine and purified according to general procedure E to furnish 0.12 g of the title compound in 93% yield. $^1$H NMR (500 MHz, CDCl$_3$) δ 7.69 (d, J=9.1 Hz, 1H), 7.38 (m, 6H), 6.95 (d, J 2.4 Hz, 1H), 6.16 (s, br, 1H), 4.86 (d, J=5.2 Hz, 2H), 3.86 (s, 3H). $^{13}$C NMR (126 MHz, CDCl$_3$) δ 160.1, 157.7, 155.5, 146.1, 137.5, 129.3, 128.9, 128.4, 128.0, 124.4, 113.6, 100.5, 55.8, 45.8. R$_f$=0.63 (DCM/MeOH 10:1).

N$^4$-Benzyl-6-methoxy-N$^2$-methylquinazoline-2,4-diamine (12)

0.10 g (0.33 mmol) N-benzyl-2-chloro-6-methoxyquinazolin-4-amine was reacted with methylamine and purified according to general procedure F to furnish 85.0 mg of the title compound as a beige crystalline solid in 78% yield. $^1$H NMR (500 MHz, DMSO) δ 8.74 (s, br, 1H), 7.82 (s, 1H), 7.61 (d, J=6.7 Hz, 2H), 7.57-7.38 (m, 5H), 6.66 (s, 1H), 4.96 (s, 2H), 4.02 (s, 3H), 3.02 (s, 3H). HRMS: m/z calculated for C$_{17}$H$_{19}$N$_4$O [M+H]+ 295.1553; found 295.1543. R$_f$=0.29 (DCM/MeOH 10:1).

N-Benzyl-2,7-dichloroquinazolin-4-amine 0.20 g (0.86 mmol) of 2,4,7-trichloroquinazoline was reacted with benzylamine and purified according to general procedure E to furnish 0.26 g of the title compound in 98% yield. $^1$H NMR (500 MHz, CDCl$_3$) δ 7.74 (s, 1H), 7.62 (d, J=8.8 Hz, 1H), 7.42-7.32 (m, 6H), 6.18 (s, br, 1H), 4.85 (d, J=5.2 Hz, 2H). $^{13}$C NMR (126 MHz, CDCl$_3$) δ 160.4, 158.8, 151.7, 139.8, 137.0, 129.0, 128.4, 128.2, 127.1, 127.0, 122.2, 111.5, 45.9. R$_f$=0.66 (DCM/MeOH 10:1).

N$^4$-Benzyl-7-chloro-N$^2$-methylquinazoline-2,4-diamine (13)

0.25 g (0.82 mmol) N-benzyl-2,7-dichloroquinazolin-4-amine was reacted with methylamine and purified according to general procedure F to furnish 77.0 mg of the title compound as a beige crystalline solid in 48/% yield. $^1$H NMR (500 MHz, CD$_3$OD) δ 7.85 (d, J=8.7 Hz, 1H), 7.42-7.28 (m, 5H), 7.21 (d, J=10.6, 1H), 7.03 (d, J=8.7, 1H), 4.78 (s, 2H), 2.93 (s, 3H). HRMS: m/z calculated for C$_{16}$H$_{16}$ClN$_4$ [M+H]+ 299.1058; found 299.1046. R$_f$=0.38 (DCM/MeOH 10:1).

N-Benzyl-7-bromo-2-chloroquinazolin-4-amine 0.10 g (0.36 mmol) of 7-bromo-2,4-dichloroquinazoline was reacted with benzylamine and purified according to general procedure E to furnish 0.12 g of the title compound in 97% yield. $^1$H NMR (500 MHz, CDCl$_3$) δ 7.94 (s, 1H), 7.53 (s, 2H), 7.43-7.33 (m, 5H), 6.1 (s, br, 1H) 4.85 (d, J=5.3 Hz, 2H). $^{13}$C NMR (126 MHz, CDCl$_3$) δ 159.6, 158.0, 149.7, 138.3, 136.9, 129.7, 129.0, 128.4, 128.3, 123.4, 119.4, 114.4, 45.9. R$_f$=0.71 (DCM/MeOH 10:1).

N$^4$-Benzyl-7-bromo-N$^2$-methylquinazoline-2,4-diamine (14)

0.11 g (0.33 mmol) N-benzyl-7-bromo-2-chloroquinazolin-4-amine was reacted with methylamine and purified according to general procedure F to furnish 90.0 mg of the title compound as a beige crystalline solid in 79% yield. $^1$H NMR (500 MHz, DMSO-d$_6$) δ 8.70 (s, 1H), 8.20 (d, J=9.0 Hz, 1H), 7.56 (dd, J=27.3, 7.7 Hz, 5H), 7.41 (dd, J=29.9, 7.6 Hz, 2H), 6.91 (s, 1H), 4.92 (s, 2H), 3.71 (s, 1H), 3.01 (s, 3H).

HRMS: m/z calculated for $C_{16}H_{16}BrN_4$ [M+H]+ 343.0553; found 343.0543. $R_f$=0.58 (DCM/MeOH 10:1).

N-Benzyl-2-chloro-7-methylquinazolin 0.10 g (0.47 mmol) of 2,4-dichloro-7-methylquinazoline was reacted with benzylamine and purified according to general procedure E to furnish 0.12 g of the title compound in 96% yield. $^1$H NMR (500 MHz, CDCl$_3$) δ 7.57 (d, J=8.4 Hz, 1H), 7.54 (s, 1H), 7.42-7.31 (m, 5H), 7.27-7.24 (m, 1H), 4.85 (d, J=5.3 Hz, 2H), 2.49 (s, 3H). $^{13}$C NMR (126 MHz, CDCl$_3$) δ 160.6, 157.7, 151.1, 144.5, 137.4, 128.9, 128.3, 128.1, 127.2, 120.6, 111.0, 45.7, 28.4, 21.9. $R_f$=0.68 (DCM/MeOH 10:1).

$N^4$-Benzyl-$N^2$,7-dimethylquinazoline-2,4-diamine (15)

0.10 g (0.35 mmol) N-benzyl-2-chloro-7-methylquinazolin was reacted with methylamine and purified according to general procedure F to furnish 77.0 mg of the title compound as a beige crystalline solid in 76% yield. $^1$H NMR (500 MHz, CDCl$_3$) δ 7.41-7.34 (m, 5H), 7.31 (d, J=6.9 Hz, 2H), 6.89 (d, J=8.2 Hz, 1H), 4.80 (d, J=5.4 Hz, 2H), 3.06 (d, J=5.0 Hz, 3H), 2.41 (s, 3H). HRMS: m/z calculated for $C_{17}H_{19}N_4$ [M+H]+ 279.1604; found 279.1597. $R_f$=0.47 (DCM/MeOH 10:1).

$N^4$-Methyl-$N^2$-phenethylquinazoline-2,4-diamine (16)

0.10 g (0.52 mmol) of 2-chloro-N-methylquinazolin-4-amine was reacted with phenethylamine and purified according to general procedure F to furnish 55.0 mg of the title compound as a beige crystalline solid in 55% yield. $^1$H NMR (500 MHz, Chloroform-d) δ 7.63 (d, J=8.2 Hz, 1H), 7.53-7.44 (m, 2H), 7.29 (q, J=6.4, 5.1 Hz, 2H), 7.27-7.18 (m, 3H), 7.03 (td, J=7.1, 6.1, 1.7 Hz, 1H), 6.46 (s, 1H), 5.36 (s, 1H), 3.79 (t, J=7.4 Hz, 2H), 3.09 (s, 3H), 2.95 (t, J=7.3 Hz, 2H). HRMS: m/z calculated for $C_{17}H_{19}N_4$ [M+H]+ 279.1604; found 279.1602. $R_f$=0.40 (DCM/MeOH 10:1).

6-Chloro-$N^4$-methyl-$N^2$-phenethylquinazoline-2,4-diamine (17)

90.0 mg (0.39 mmol) 2,6-dichloro-N-methylquinazolin-4-amine was reacted with phenethylamine and purified according to general procedure F to furnish 55.0 mg of the title compound as a beige crystalline solid in 48% yield. $^1$H NMR (400 MHz, CDCl$_3$) δ 7.44-7.40 (m, 2H), 7.35 (d, J=9.4 Hz, 1H), 7.31-7.24 (m, 4H), 7.23-7.17 (m, 1H), 5.53 (s, 1H), 5.08 (s, 1H), 3.75, (q, J=6.8 Hz, 2 Hz), 3.08 (d, J=4.8 Hz, 3H), 2.93 (t, J=7.2 Hz, 2H). HRMS: m/z calculated for $C_{17}H_{18}ClN_4$ [M+H]+ 312.8073; found 312.7996. $R_f$=0.38 (DCM/MeOH 10:1).

6-Methoxy-$N^4$-methyl-$N^2$-phenethylquinazoline-2,4-diamine (18)

60.0 mg (0.20 mmol) 2,4-dichloro-6-methoxyquinazoline was reacted with phenethylamine and purified according to general procedure F to furnish 17.0 mg of the title compound as a beige crystalline solid in 23% yield. $^1$H NMR (500 MHz, CDCl$_3$) δ 7.43 (d, J=9.1 Hz, 1H), 7.34-7.25 (m, 4H), 7.25-7.18 (m, 2H), 6.88 (d, J=2.7 Hz, 1H), 5.75 (s, 1H), 5.06 (s, 1H), 3.81 (s, 3H), 3.80-3.75 (m, 2H), 3.14 (d, J=4.7 Hz, 3H), 2.96 (t, J=7.2 Hz, 2H). $R_f$=0.29 (DCM/MeOH 10:1).

6-Bromo-$N^4$-methyl-$N^2$-phenethylquinazoline-2,4-diamine (19)

65.0 mg (0.24 mmol) 6-bromo-2-chloro-N-methylquinazolin-4-amine was reacted with phenethylamine and purified according to general procedure F to furnish 31.0 mg of the title compound as a beige crystalline solid in 37% yield. $^1$H NMR (500 MHz, CDCl$_3$) δ 7.64 (d, J=2.2 Hz, 1H), 7.57 (dd, J=8.9, 2.2 Hz, 1H), 7.32 (t, J=7.5 Hz, 3H), 7.29-7.25 (m, 2H), 7.25-7.21 (m, 1H), 5.72 (s, 1H), 5.28 (s, 1H), 3.77 (q, J=7.0 Hz, 2H), 3.11 (d, J=4.6 Hz, 3H), 2.96 (t, J=7.2 Hz, 2H). HRMS: m/z calculated for $C_{17}H_{18}BrN_4$ [M+H]+ 357.0709; found 357.0714. $R_f$=0.59 (DCM/MeOH 10:1).

$N^4$,6-Dimethyl-$N^2$-phenethylquinazoline-2,4-diamine (20)

75.0 mg (0.36 mmol) 2-chloro-N,6-dimethylquinazolin-4-amine was reacted with phenethylamine and purified according to general procedure F to furnish 49.0 mg of the title compound as a beige crystalline solid in 46% yield. $^1$H NMR (500 MHz, CDCl$_3$) δ 7.39 (d, J=8.3 Hz, 1H), 7.35 (d, J=8.5 Hz, 1H), 7.33-7.28 (m, 2H), 7.26 (d, J=7.4 Hz, 2H), 7.21 (d, J=6.5 Hz, 2H), 6.28 (s, 1H), 5.37 (s, 1H), 3.78 (t, J=6.5 Hz 2H), 3.09 (s, 3H), 2.96 (t, J=6.5 Hz, 2H), 2.34 (s, 3H). HRMS: m/z calculated for $C_{18}H_{21}N_4O$ [M+H]+ 293.1761; found 293.1764. $R_f$=0.34 (DCM/MeOH 10:1).

$N^2$-Benzyl-$N^4$-methyl-6-vinylquinazoline-2,4-diamine (22)

50 mg (0.14 mmol) of $N^2$-benzyl-6-bromo-$N^4$-methylquinazoline-2,4-diamine was reacted with commercially available vinyl boronic acid dibutyl ester and purified according to procedure A to furnish 13 mg of the title compound as a yellow solid in 31% yield. $^1$H NMR (500 MHz, Methanol-d$_4$) δ 7.84 (d, J=1.9 Hz, 1H), 7.68 (dd, J=8.7, 1.9 Hz, 1H), 7.38 (d, J=6.9 Hz, 2H), 7.29 (t, J=7.6 Hz, 3H), 7.21 (t, J=7.3 Hz, 1H), 6.75 (dd, J=17.6, 11.0 Hz, 1H), 5.78 (d, J=17.6 Hz, 1H), 5.21 (d, J=11.0 Hz, 1H), 4.67 (s, 2H), 3.04 (s, 3H). HRMS: m/z calculated for $C_{18}H_{19}N_4$ [M+H]$^+$ 291.1604; found 291.1633. $R_f$=0.33 (DCM/MeOH 10:1).

$N^2$-Benzyl-6-ethyl-$N^4$-methylquinazoline-2,4-diamine (23)

10 mg (0.03 mmol) of $N^2$-benzyl-$N^4$-methyl-6-vinylquinazoline-2,4-diamine was reacted with palladium on carbon in a 10 mL round bottom flask affixed with a hydrogen balloon and purified according to procedure B to furnish 7 mg of the title compound as a yellow solid in 70% yield. $^1$H NMR (500 MHz, DMSO-d$_6$) δ 7.67 (d, J=8.6 Hz, 1H), 7.62 (s, 1H), 7.52 (d, J=7.38 Hz, 2H), 7.36 (t, J=7.4 Hz, 2H), 7.33 (d, J=8.6 Hz, 1H), 7.25 (t, J=7.4 Hz, 1H), 4.64 (d, J=5.9 Hz, 2H), 2.98 (d, J=5.2 Hz, 3H), 2.65 (q, J=7.3 Hz, 2H), 1.31 (t, J=7.3 Hz, 3H). HRMS: m/z calculated for $C_{18}H_{21}N_4$ [M+H]$^+$ 293.1761; found 293.1768. $R_f$=0.31 (DCM/MeOH 9:1).

$N^2$-Benzyl-$N^4$-methyl-6-(prop-1-en-2-yl)quinazoline-2,4-diamine (24)

80 mg (0.23 mmol) of $N^2$-benzyl-6-bromo-$N^4$-methylquinazoline-2,4-diamine was reacted with commercially available isopentyl pinacol boronic ester and purified according to procedure A to furnish 22 mg of the title compound as a yellow solid in 31% yield. $^1$H NMR (500 MHz, DMSO-$d_6$) δ 8.05-7.90 (m, 3H), 7.52 (d, J=7.4 Hz, 2H), 7.36 (t, J=7.4 Hz, 2H), 7.25 (t, J=7.4 Hz, 1H), 5.68 (s, 1H), 5.32 (s, 1H), 4.64 (d, J=5.9 Hz, 2H), 2.99 (d, J=5.2 Hz, 3H), 2.32 (s, 3H). HRMS: m/z calculated for $C_{19}H_{21}N_4$ [M+H]$^+$ 305.1761; found 305.1766. $R_f$=0.31 (DCM/MeOH 9:1).

$N^2$-Benzyl-6-isopropyl-$N^4$-methylquinazoline-2,4-diamine (25)

10 mg (0.03 mmol) of $N^2$-benzyl-$N^4$-methyl-6-(prop-1-en-2-yl)quinazoline-2,4-diamine was reacted with palladium on carbon in a 10 mL round bottom flask affixed with a hydrogen balloon and purified according to procedure B to furnish 5 mg of the title compound as a yellow solid in 50% yield. $^1$H NMR (500 MHz, DMSO-$d_6$) δ 7.69 (s, 1H), 7.57-7.48 (m, 4H), 7.36 (t, J=7.4 Hz, 2H), 7.25 (t, J=7.4 Hz, 1H), 4.64 (d, J=5.9 Hz, 2H), 3.14 (sept, J=6.9 Hz, 1H), 2.99 (d, J=5.2 Hz, 3H), 1.32 (d, J=6.9 Hz, 6H). HRMS: m/z calculated for $C_{19}H_{23}N_4$ [M+H]$^+$ 307.1917; found 307.1643. $R_f$=0.28 (DCM/MeOH 9:1).

(E)-$N^2$-Benzyl-$N^4$-methyl-6-(pent-1-en-1-yl)quinazoline-2,4-diamine (26)

80 mg (0.23 mmol) of $N^2$-benzyl-6-bromo-$N^4$-methylquinazoline-2,4-diamine was reacted with commercially available (E)-1-Pentenyl pinacol boronic ester and purified according to procedure A to furnish 24 mg of the title compound as a yellow solid in 31% yield. $^1$H NMR (500 MHz, DMSO-$d_6$) δ 8.11 (s, 1H), 7.65-7.56 (m, 2H), 7.52 (d, J=7.4 Hz, 2H), 7.36 (t, J=7.4 Hz, 2H), 7.25 (t, J=7.4 Hz, 1H), 6.93-6.78 (m, 2H), 4.64 (d, J=5.9 Hz, 2H), 2.99 (d, J=5.2 Hz, 3H), 2.17 (td, J=7.4, 6.7 Hz, 2H), 1.48 (sext, J=7.4 Hz, 2H), 0.95 (t, J=7.2 Hz, 3H). HRMS: m/z calculated for $C_{21}H_{25}N_4$ [M+H]$^+$ 333.2074; found 333.2064. $R_f$=0.33 (DCM/MeOH 9:1).

$N^2$-Benzyl-$N^4$-methyl-6-pentylquinazoline-2,4-diamine (27)

11 mg (0.03 mmol) of (E)-$N^2$-benzyl-$N^4$-methyl-6-(pent-1-en-1-yl)quinazoline-2,4-diamine was reacted with palladium on carbon and purified according to procedure B to furnish 7 mg of the title compound as a yellow solid in 70% yield. $^1$H NMR (500 MHz, Methanol-$d_4$) δ 7.66 (d, J=1.8 Hz, 1H), 7.42 (dd, J=8.5, 1.9 Hz, 1H), 7.38 (d, J=7.2 Hz, 2H), 7.29 (td, J=8.5, 8.0, 2.5 Hz, 3H), 7.21 (t, J=7.3 Hz, 1H), 4.67 (s, 2H), 3.05 (s, 3H), 2.66 (t, J=7.7 Hz, 2H), 1.65 (p, J=7.5 Hz, 2H), 1.41-1.25 (m, 4H), 0.91 (t, J=6.9 Hz, 3H). HRMS: m/z calculated for $C_{21}H_{27}N_4$ [M+H]$^+$ 335.2230; found 335.2083.

$N^2$-Benzyl-6-(cyclopent-1-en-1-yl)-$N^4$-methylquinazoline-2,4-diamine (28)

80 mg (0.23 mmol) of $N^2$-benzyl-6-bromo-$N^4$-methylquinazoline-2,4-diamine was reacted with commercially available 1-cyclopentenyl boronic acid pinacol ester and purified according to procedure A to furnish 8 mg of the title compound as a yellow solid in 10% yield. $^1$H NMR (500 MHz, CDCl$_3$) δ 7.74 (dd, J=8.7, 2.0 Hz, 1H), 7.49-7.36 (m, 7H), 7.32 (t, J=7.4 Hz, 2H), 7.29-7.22 (m, 3H), 6.18 (p, J=2.1 Hz, 1H), 5.83 (s, 1H), 4.74 (d, J=4.9 Hz, 2H), 3.12 (d, J=4.6 Hz, 3H), 2.74 (dp, J=7.7, 2.4 Hz, 2H), 2.56 (tq, J=7.5, 2.5 Hz, 2H), 2.05 (p, J=7.5 Hz, 2H). HRMS: m/z calculated for $C_{21}H_{23}N_4$ [M+H]$^+$ 331.1917; found 331.1995. $R_f$=0.33 (DCM/MeOH 9:1).

$N^2$-Benzyl-6-(cyclohex-1-en-1-yl)-$N^4$-methylquinazoline-2,4-diamine (29)

80 mg (0.14 mmol) of $N^2$-benzyl-6-bromo-$N^4$-methylquinazoline-2,4-diamine was reacted with commercially available cyclohexenyl boronic acid and purified according to procedure A to furnish 11 mg of the title compound as a yellow solid in 14% yield. $^1$H NMR (500 MHz, Methanol-$d_4$) δ 7.84 (d, J=2.0 Hz, 1H), 7.67 (dd, J=8.7, 2.1 Hz, 1H), 7.38 (d, J=7.2 Hz, 2H), 7.30 (dt, J=9.9, 7.7 Hz, 3H), 7.22 (t, J=7.3 Hz, 1H), 6.18 (tt, J=4.1, 1.7 Hz, 1H), 4.68 (s, 2H), 3.06 (s, 3H), 2.45 (tq, J=6.4, 2.2 Hz, 2H), 2.23 (ddt, J=8.4, 6.4, 3.3 Hz, 2H), 1.85-1.78 (m, 2H), 1.71-1.64 (m, 2H). HRMS: m/z calculated for $C_{22}H_{25}N_4$ [M+H]$^+$ 345.2074; found 345.2077. $R_f$=0.33 (DCM/MeOH 9:1).

$N^2$-Benzyl-6-cyclohexyl-$N^4$-methylquinazoline-2,4-diamine (30)

10 mg (0.03 mmol) of $N^2$-benzyl-6-(cyclohex-1-en-1-yl)-M-methylquinazoline-2,4-diamine was reacted with palladium on carbon and purified according to procedure B to furnish 8 mg of the title compound as a yellow solid in 80% yield. $^1$H NMR (500 MHz, Methanol-$d_4$) δ 7.69 (d, J=1.9 Hz, 1H), 7.45 (dd, J=8.5, 2.0 Hz, 1H), 7.38 (d, J=7.0 Hz, 2H), 7.29 (td, J=8.3, 7.8, 2.1 Hz, 3H), 7.21 (t, J=7.4 Hz, 1H), 4.67 (s, 2H), 3.05 (s, 3H), 2.56 (tt, J=11.7, 3.2 Hz, 1H), 1.91-1.82 (m, 5H), 1.81-1.74 (m, 1H), 1.53 (dd, J=12.4, 2.9 Hz, 1H), 1.50-1.45 (m, 2H), 1.43 (t, J=3.3 Hz, 1H). HRMS: m/z calculated for $C_{22}H_{27}N_4$ [M+H]$^+$ 347.2230; found 347.2231. $R_f$=0.32 (DCM/MeOH 9:1).

$N^2$-Benzyl-$N^4$-methyl-6-phenylquinazoline-2,4-diamine (31)

50 mg (0.14 mmol) of $N^2$-benzyl-6-bromo-$N^4$-methylquinazoline-2,4-diamine was reacted with commercially available phenyl boronic acid and purified according to procedure A to furnish 11 mg of the title compound as a yellow solid in 22% yield. $^1$H NMR (500 MHz, Methanol-$d_4$) δ 8.17 (s, 1H), 7.91-7.85 (m, 1H), 7.68 (d, J=7.7 Hz, 2H), 7.48-7.38 (m, 5H), 7.33 (q, J=7.6 Hz, 3H), 7.24 (t, J=7.5 Hz, 1H), 4.71 (s, 2H), 3.08 (s, 3H). HRMS: m/z calculated for $C_{22}H_{21}N_4$ [M+H]$^+$ 341.1761; found 341.1763. $R_f$=0.36 (DCM/MeOH 10:1.

$N^2$-Benzyl-6-(furan-2-yl)-$N^4$-methylquinazoline-2,4-diamine (32)

50 mg (0.14 mmol) of $N^2$-benzyl-6-bromo-$N^4$-methylquinazoline-2,4-diamine was reacted with commercially available 2-furyl boronic acid and purified according to procedure A to furnish 6 mg of the title compound as a yellow solid in 13% yield. $^1$H NMR (500 MHz, Methanol-$d_4$) δ 8.19 (d, J=1.8 Hz, 1H), 7.87 (dd, J=8.8, 1.9 Hz, 1H), 7.55 (d, J=1.8 Hz, 1H), 7.39 (d, J=7.3 Hz, 2H), 7.35 (d, J=8.8 Hz, 1H), 7.31 (dd, J=8.5, 6.8 Hz, 2H), 7.22 (t, J=7.3 Hz, 1H), 6.75 (d, J=3.3 Hz, 1H), 6.52 (dd, J=3.4, 1.8 Hz, 1H), 4.68 (s, 2H), 3.06 (s, 3H). HRMS: m/z calculated for $C_{20}H_{19}N_4O$ [M+H]$^+$ 331.1553; found 331.1549. $R_f$=0.43 (DCM/MeOH 10:1).

Antibacterial Activity Assessment.

MIC and MBC assays were performed in this study as documented by us previously.[17,23,24,25] The *A. baumannii* strains used are detailed in Table 7.

Biofilm Eradication Determination Assay.

These assays were performed as described by us previously,[26,24] as follows. Each of the *A. baumannii* strains were grown overnight in Mueller Hinton Broth (MHB). The next day these were used to seed fresh MHB to an $OD_{600}$ of 0.5, with 150 µL then added to the wells of a 96 well plate and grown for 24 hours at 37° C. After 24 hours, the planktonic bacteria were carefully removed and fresh MHB was added with increasing concentrations of lead quinazolines. After incubation at 37° C. for 24 hours, planktonic cells were removed and biofilms were washed three times with phosphate buffered saline (PBS). Biofilms were then resuspended in PBS and plated for cell viability on tryptic soy agar. Biofilm recovery was assessed compared to no drug controls, and determined as percent eradication. This was used to determine $MBEC_{90}$ values (Minimal Biofilm Eradication Concentration), where the viability of cells within the biofilm was reduced by 90%.

Investigating the Mechanism of Action of Quinazoline-Based Compounds.

To evaluate the effect quinazolines have on DHFR reduction of dihydrofolic acid, a tetrahydrofolic acid assay was performed as described by us previously.[17] *A. baumannii* strain 1403 was grown overnight in LB, and then diluted 1:1000 into fresh media. These cultures were then seeded into a sterile 96-well plate with tetrahydrofolic acid added at concentrations ranging from 0 to 225 µM. Lead quinazoline 25 was then added at 1×, 2×, and 5× the MIC and cultures were incubated at 37° C. for 18 hours. MICs were determined and used to assess whether the addition of tetrahydrofolic acid rescued *A. baumannii* growth from quinazoline inhibition. Assays were repeated in triplicate, alongside trimethoprim and sulfamethoxazole controls.

Serial Passage Assay.

In order to test potential resistance towards the quinazolines, a serial passage assay was performed alongside control compounds (Sulfamethoxazole and Trimethoprim), as described by us previously.[24] *A. baumannii* strain 1403 was grown overnight in LB media at 37° C. The next day cultures were diluted 1:100 in fresh media and seeded into a 96-well plate. Lead quinazolines or control agents were added to respective wells at half MIC concentrations. Plates were then incubated for 24 hours at 37° C., followed by the removal of aliquots from these cultures to inoculate fresh media (1:100 dilution) containing compounds at a 2-fold higher concentrations. These were then grown overnight, and the procedure repeated for a total of eight days. The cultures were observed for a lack of growth, indicating strains were no longer able to resist the action of a given compound. Each experiment was performed in triplicate, yielding identical results.

HepG2 Cytotoxicity.

Cytotoxicity assays were performed using human HepG2 cells (human liver epithelial with hepatocellular carcinoma), as described by us previously.[17,24] Cells were cultured in Dulbecco's modified eagle medium (DMEM), supplemented with 10% fetal bovine serum and 1% penicillin-streptomycin for 3 days at 37° C. and 5% $CO_2$. Cells were then diluted to $1 \times 10^5$ ml$^{-1}$ using fresh DMEM and added to 96 well tissue culture plates at a volume of 100 µL. Plates were incubated for 24 hours at 37° C. and 5% $CO_2$, allowing the cells to adhere to the plastic. After this time, media was carefully removed and 200 µL fresh DMEM added with test compounds at concentrations: 0, 1, 2, 5, 10, 15, 30, and 50 µM. Plates were then incubated for 48 hours at 37° C. and 5% $CO_2$. After 48 hours the DMEM was removed and 100 µL of new media was added containing MTT (3-(4, 5-dimethylthiazol-2-yl)-2, 5-diphenyltetrazolium bromide), followed by incubation for four hours at 37° C. and 5% $CO_2$. After 4 h, 75 µL of media was removed, replaced with 50 µL of 16% w/v SDS and DMSO followed by incubation for ten minutes at 37° C. to solubilize any formazan produced. A Biotek plate reader was used to measure the absorbance of formazan production at 540 nM. Lead compounds were solvated in 100% DMSO for these studies, which served as the negative control. $LD_{50}$ values were determined for each compound by comparison to vehicle only controls.

Hemolysis Assay.

A hemolysis assay was performed using whole human blood (Bioreclamation), as described previously.[24] Briefly, human red blood cells (hRBCs) were resuspended in 20% v/v 1×HA buffer (4.25 mL 10% NaCl; 1 mL $CaCl_2$) in 50 mL sterile water), before lead compounds were added at 2 µM, 10 µM and 20 µM, in a final volume of 100 µL. Cells were incubated for 15 minutes at 37° C. before being centrifuged at 5,500 g for 1 minute to pellet non-lysed hRBCs. The supernatant was removed, added to a 96-well Microtiter plate and the $OD_{543}$ read using a BioTek Synergy2 plate reader. The negative control was vehicle only (DMSO), and the positive control was 1% triton X-100. Assays were performed in triplicate, with data displayed as percent hemolysis compared to controls, defined as: Percent Hemolysis=($OD_{543}$ test sample–$OD_{543}$ no drug control)/($OD_{543}$ Triton X-100–$OD_{543}$ no drug control)×100.

In Vivo Efficacy Testing Using a Murine Model of Lethal Peritonitis.

A murine model of lethal peritonitis was used to demonstrate the effectiveness of the lead quinazolines to clear bacterial infections, as described by us previously.[24] Six mice per group were infected via I.P. injection with $7.5 \times 10^8$ CFU mL$^{-1}$ of *A. baumannii* 1646 (Table 7) in PBS containing 5% mucin. After 1 h, mice were inoculated by I.P. injection to the left side of the abdomen with either 2 mg/kg of lead agent 25 (test group); 30 mg/kg Tigecycline (positive control); or vehicle alone (45% w/v (2-hydroxypropyl)-β-cyclodextrin in water (negative control). Mice were monitored twice daily for five days to assess mortality. All animal studies received written approval after review by the Institutional Animal Care & Use Committee in the Division of Comparative Medicine & Division of Research Integrity & Compliance at the University of South Florida. The clinical endpoint was reached for this study when the mice reached a pre-moribund state. Characteristics of pre-moribund state include: hunched posture, rapid, shallow and/or labored breathing, ruffled fur, lethargy, failure to respond to stimuli, soiled anogenital area, paralysis, paresis, head tilt, circling, vocalizations, non-purposeful movements, and/or were unable to eat or drink. Those mice reaching this state prior to the completion of the 5-day infection period were euthanized. The number of mice surviving between control and treatment groups was compared and analyzed for statistical significance using a log-rank (Mantel-Cox) test.

REFERENCES FOR EXAMPLE 1

1. Perez, F.; Hujer, A. M.; Hujer, K. M.; Decker, B. K.; Rather, P. N.; Bonomo, R. A., Global Challenge of Multidrug-Resistant *Acinetobacter baumannii*. *Antimicrobial Agents and Chemotherapy* 2007, 51 (10), 3471-3484.

2. Necati Hakyemez, I.; Kucukbayrak, A.; Tas, T.; Burcu Yikilgan, A.; Akkaya, A.; Yasayacak, A.; Akdeniz, H., Nosocomial *Acinetobacter baumannii* Infections and Changing Antibiotic Resistance. *Pak J Med Sci* 2013, 29 (5), 1245-8.

3. (a) Sebeny, Peter J.; Riddle, Mark S.; Petersen, K., *Acinetobacter baumannii* Skin and Soft-Tissue Infection Associated with War Trauma. *Clinical Infectious Diseases* 2008, 47 (4), 444-449; (b) Akers, K. S.; Mende, K.; Cheatle, K. A.; Zera, W. C.; Yu, X.; Beckius, M. L.; Aggarwal, D.; Li, P.; Sanchez, C. J.; Wenke, J. C.; Weintrob, A. C.; Tribble, D. R.; Murray, C. K., Biofilms and persistent wound infections in United States military trauma patients: a case—control analysis. *BMC Infectious Diseases* 2014, 14 (1), 190.

4. Manchanda, V.; Sanchaita, S.; Singh, N., Multidrug resistant *acinetobacter*. *J Glob Infect Dis* 2010, 2 (3), 291-304.

5. Boucher, Helen W.; Talbot, George H.; Bradley, John S.; Edwards, John E.; Gilbert, D.; Rice, Louis B.; Scheld, M.; Spellberg, B.; Bartlett, J., Bad Bugs, No Drugs: No ESKAPE! An Update from the Infectious Diseases Society of America. *Clinical Infectious Diseases* 2009, 48 (1), 1-12.

6. Falagas, M. E.; Bliziotis, I. A., Pandrug-resistant Gram-negative bacteria: the dawn of the post-antibiotic era? *International Journal of Antimicrobial Agents* 2007, 29 (6), 630-636.

7. Van Horn, K. S.; Zhu, X.; Pandharkar, T.; Yang, S.; Vesely, B.; Vanaerschot, M.; Dujardin, J.-C.; Rijal, S.; Kyle, D. E.; Wang, M. Z.; Werbovetz, K. A.; Manetsch, R., Antileishmanial Activity of a Series of $N^2,N^4$-Disubstituted Quinazoline-2,4-diamines. *Journal of medicinal chemistry* 2014, 57 (12), 5141-5156.

8. Zhu, X.; Van Horn, K. S.; Barber, M. M.; Yang, S.; Wang, M. Z.; Manetsch, R.; Werbovetz, K. A., SAR refinement of antileishmanial N2,N4-disubstituted quinazoline-2,4-diamines. *Bioorganic & medicinal chemistry* 2015, 23 (16), 5182-5189.

9. Wang, D.; Gao, F., Quinazoline derivatives: synthesis and bioactivities. *Chem Cent J* 2013, 7 (1), 95.

10. Alagarsamy, V.; Raja Solomon, V.; Dhanabal, K., Synthesis and pharmacological evaluation of some 3-phenyl-2-substituted-3H-quinazolin-4-one as analgesic, anti-inflammatory agents. *Bioorganic & Medicinal Chemistry* 2007, 15 (1), 235-241.

11. Chandregowda, V.; Kush, A. K.; Chandrasekara Reddy, G., Synthesis and in vitro antitumor activities of novel 4-anilinoquinazoline derivatives. *European Journal of Medicinal Chemistry* 2009, 44 (7), 3046-3055.

12. Rohini, R.; Muralidhar Reddy, P.; Shanker, K.; Hu, A.; Ravinder, V., Antimicrobial study of newly synthesized 6-substituted indolo[1,2-c]quinazolines. *European Journal of Medicinal Chemistry* 2010, 45 (3), 1200-1205.

13. Alvarado, M.; Barceló, M.; Carro, L.; Masaguer, C. F.; Raviña, E., Synthesis and Biological Evaluation of New Quinazoline and Cinnoline Derivatives as Potential Atypical Antipsychotics. *Chemistry & Biodiversity* 2006, 3 (1), 106-117.

14. Malamas, M. S.; Millen, J., Quinazolineacetic acids and related analogs as aldose reductase inhibitors. *Journal of Medicinal Chemistry* 1991, 34 (4), 1492-1503.

15. Kung, P. P.; Casper, M. D.; Cook, K. L.; Wilson-Lingardo, L.; Risen, L. M.; Vickers, T. A.; Ranken, R.; Blyn, L. B.; Wyatt, J. R.; Cook, P. D.; Ecker, D. J., Structure-activity relationships of novel 2-substituted quinazoline antibacterial agents. *J Med Chem* 1999, 42 (22), 4705-13.

16. Harris, N. V.; Smith, C.; Bowden, K., Antifolate and antibacterial activities of 5-substituted 2,4-diaminoquinazolines. *J Med Chem* 1990, 33 (1), 434-44.

17. Van Horn, K. S.; Burda, W. N.; Fleeman, R.; Shaw, L. N.; Manetsch, R., Antibacterial Activity of a Series of N2,N4-Disubstituted Quinazoline-2,4-diamines. *Journal of Medicinal Chemistry* 2014, 57 (7), 3075-3093.

18. Lam, T.; Hilgers, M. T.; Cunningham, M. L.; Kwan, B. P.; Nelson, K. J.; Brown-Driver, V.; Ong, V.; Trzoss, M.; Hough, G.; Shaw, K. J.; Finn, J., Structure-Based Design of New Dihydrofolate Reductase Antibacterial Agents: 7-(Benzimidazol-1-yl)-2,4-diaminoquinazolines. *Journal of Medicinal Chemistry* 2014, 57 (3), 651-668.

19. DeGraw, J. I.; Brown, V. H.; Colwell, W. T.; Morrison, N. E., Potential antileprotic agents. 3. Inhibition of mycobacterial dihydrofolic reductase by 2,4-diamino-5-methyl-6-alkylquinazolines. *Journal of Medicinal Chemistry* 1974, 17 (7), 762-764.

20. Blaney, J. M.; Hansch, C.; Silipo, C.; Vittoria, A., Structure-activity relationships of dihydrofolated reductase inhibitors. *Chemical Reviews* 1984, 84 (4), 333-407.

21. Miyaura, N.; Suzuki, A., Palladium-Catalyzed Cross-Coupling Reactions of Organoboron Compounds. *Chemical Reviews* 1995, 95 (7), 2457-2483.

22. Ayral-Kaloustian, S.; Chen, L.; Chen, Z.; Curran, K.; Dehnhardt, C.; Santos, E. D.; Dos Santos, O.; Venkatesan, A. M. Amino-substituted quinazoline derivatives as inhibitors of β-cantenin/TCF-4 pathway and cancer treatment agents. 2009.

23. Cormier, R.; Burda, W. N.; Harrington, L.; Edlinger, J.; Kodigepalli, K. M.; Thomas, J.; Kapolka, R.; Roma, G.; Anderson, B. E.; Turos, E.; Shaw, L. N., Studies on the antimicrobial properties of N-acylated ciprofloxacins. *Bioorganic & medicinal chemistry letters* 2012, 22 (20), 6513-6520.

24. Fleeman, R.; LaVoi, T. M.; Santos, R. G.; Morales, A.; Nefzi, A.; Welmaker, G. S.; Medina-Franco, J. L.; Giulianotti, M. A.; Houghten, R. A.; Shaw, L. N., Combinatorial Libraries As a Tool for the Discovery of Novel, Broad-Spectrum Antibacterial Agents Targeting the ESKAPE Pathogens. *Journal of medicinal chemistry* 2015.

25. Burda, W. N.; Fields, K. B.; Gill, J. B.; Burt, R.; Shepherd, M.; Zhang, X. P.; Shaw, L. N., Neutral metallated and meso-substituted porphyrins as antimicrobial agents against Gram-positive pathogens. *European Journal of Clinical Microbiology & Infectious Diseases* 2011, 31 (3), 327-335.

26. von Salm, J. L.; Witowski, C. G.; Fleeman, R. M.; McClintock, J. B.; Amsler, C. D.; Shaw, L. N.; Baker, B. J., Darwinolide, a New Diterpene Scaffold That Inhibits Methicillin-Resistant *Staphylococcus aureus* Biofilm from the Antarctic Sponge *Dendrilla membranosa*. *Org Lett* 2016, 18 (11), 2596-9.

We claim:

1. A compound selected from 26, 27, 29, or 30

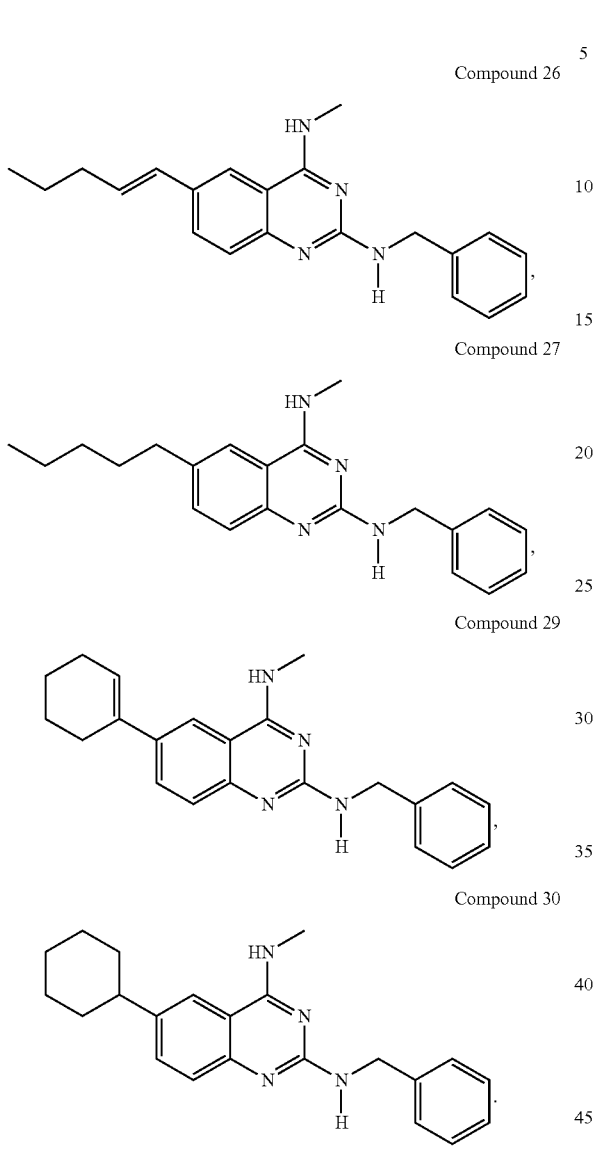

Compound 26

Compound 27

Compound 29

Compound 30

2. A pharmaceutical formulation comprising:
any one of compounds 4, 5, 26, 27, 29, or 30

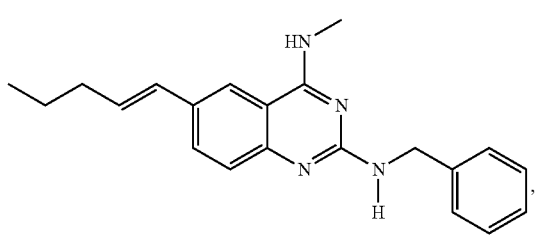

Compound 26

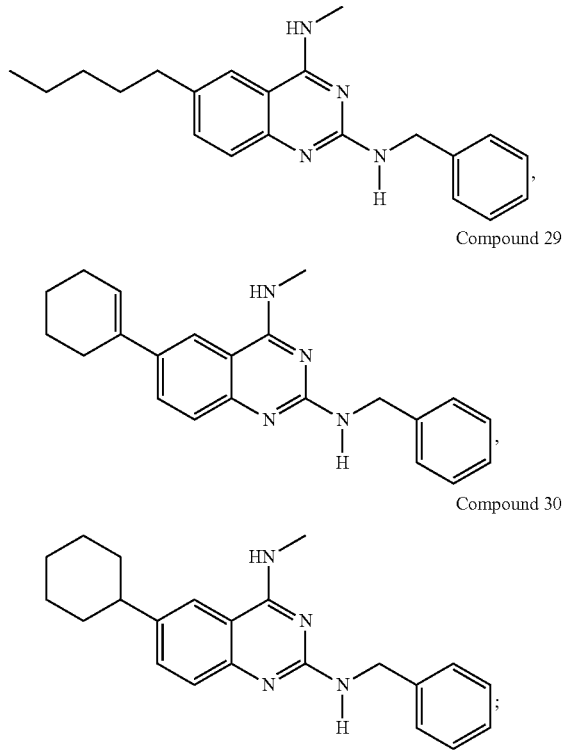

Compound 27

Compound 29

Compound 30 and
a pharmaceutically acceptable carrier.

3. The pharmaceutical formulation of claim 2, wherein any one of compounds 26, 27, 29, or 30 is included at a therapeutically effective amount sufficient to inhibit the growth, kill, amount, pathogenicity or any combination thereof of *A. baumannii*.

4. A method of treating *A. baumannii* infection in a subject in need thereof, the method comprising:
administering an amount of any one of compounds 26, 27, 29, or 30

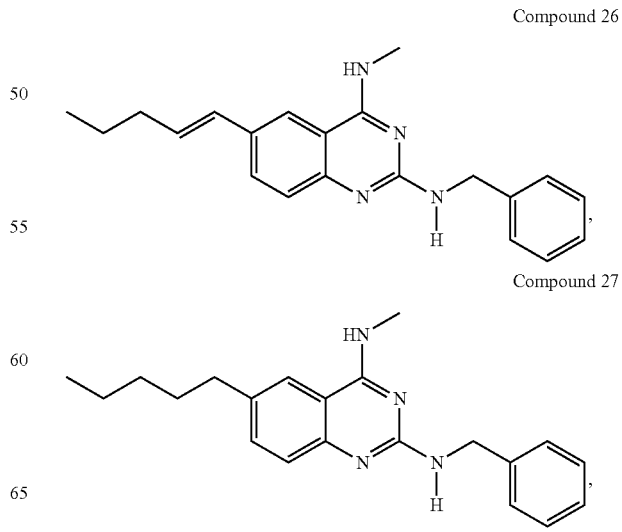

Compound 26

Compound 27

-continued

Compound 29

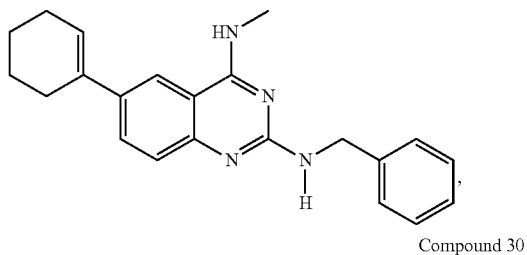

Compound 30

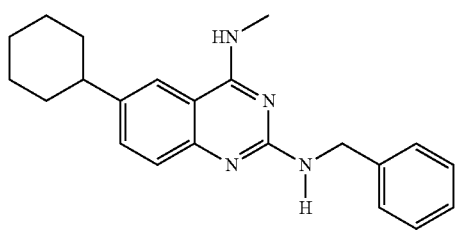

or a pharmaceutical formulation thereof to the subject in need thereof.

5. The method of claim 4, wherein the *A. baumannii* is resistant to gentamycin, polymyxinB, aztreonam, cefotaxime, ceftriaxone, tetracycline, or combinations thereof.

6. The pharmaceutical formulation of claim 2, wherein any one of compounds 26, 27, 29, or 30 is included at a therapeutically effective amount sufficient to inhibit the growth, amount, pathogenicity or any combination thereof of against a strain of *A. baumannii* that is resistant to gentamycin, polymyxinB, aztreonam, cefotaxime, ceftriaxone, tetracycline, or combinations thereof.

* * * * *